(12) United States Patent
Kilcoyne et al.

(10) Patent No.: US 6,689,056 B1
(45) Date of Patent: Feb. 10, 2004

(54) IMPLANTABLE MONITORING PROBE

(75) Inventors: John T. Kilcoyne, San Diego, CA (US); Ross Tsukashima, San Diego, CA (US); George M. Johnson, Santa Ana, CA (US); Christopher Klecher, San Diego, CA (US)

(73) Assignee: Medtronic Endonetics, Inc., Minneapolis, MN (US)

( * ) Notice: Subject to any disclaimer, the term of this patent is extended or adjusted under 35 U.S.C. 154(b) by 0 days.

(21) Appl. No.: 09/544,373

(22) Filed: Apr. 6, 2000

Related U.S. Application Data

(63) Continuation-in-part of application No. 09/287,617, filed on Apr. 7, 1999, now Pat. No. 6,285,897.

(51) Int. Cl.[7] .................................................. A61B 5/00
(52) U.S. Cl. ........................................ 600/300; 128/898
(58) Field of Search ................................. 600/300–302, 600/309; 128/897–899; 606/139, 140, 144; 623/11.11, 23.75

(56) References Cited

U.S. PATENT DOCUMENTS

| 3,133,537 A | 5/1964 | Muth |
| 3,340,866 A | 9/1967 | Nöller |
| 3,480,003 A | 11/1969 | Crites |

(List continued on next page.)

FOREIGN PATENT DOCUMENTS

| WO | WO 98/02209 | 1/1998 |
| WO | WO 01/12102 A1 | 2/2001 |

OTHER PUBLICATIONS

*An endoscopically deliverable tissue–transfixing device for securing biosensors in the gastrointestinal tract*; C. Paul Swain et al., Gastrointestinal Endoscopy, vol. 40, No. 6, 1994.

*Keeping an Eye on the Baby*, NASA Tech Briefs, Feb. 1999, www.nasatech.com.
*Miniaturized Transmitter to be Used in Efforts to Save Babies*, NASA Ames Research Center, John Bluck, Nov. 18, 1998 e–mail, Release 98–65AR.
*Ambulatory Reflux Testing*, Medtronics Sysectics, Medtronics, Inc., Mar. 9, 1999, Web page.
*Digitrapper™ MkIII Ambulatory pH Recorder*; Medtronic Brochure, 1998.
*Manometric Catheters*, Zinetics Medical, Inc. Brochure.
*Zinetics® Medical, Inc., Critical Care pH Systems*, Zinetics Medical, Inc. Brochure, ZMAC rev. 3.
*Zinetics 24M, Ambulatory pH Catheters*, Zinetics Medical, Inc., ZM24M rev/01.
*Pill–Shaped Implantable Biotelemeters*, Nasa, Sensors 2000!, Ames Research Center, http://s2k.arc.nasa.gov/.
*8.2 24–h pH–metry*, Clinical Procedures in Children, pp. 143–151.
*Implantable Biotelemetry System for Preterm Labor and Fetal Monitoring*, National Aeronautics and Space Administration, Ames Research Center.
*An ambulant porcine model of acid reflux used to evaluate endoscopic gastroplasty*, S.S. Kadirkamanathan et al., Gastrointestinal Science Research Unit, The London Hospital, pp. 782–788, 1999.
*Endoscopic Ligator, Information for Use*, C.R. Bard, Inc., Issued 7/98.

Primary Examiner—Max F. Hindenburg
Assistant Examiner—David J. McCrosky
(74) *Attorney, Agent, or Firm*—Shumaker & Sieffert, PA

(57) ABSTRACT

Disclosed is an ambulatory system for monitoring one or more physiological parameters in a body lumen, such as the esophagus. The system includes an implantable probe having a sensor for the physiological parameter and a transmitter for transmitting data to an external receiver. The probe may be used for monitoring any of various physiological parameters, including pH, temperature, and pressure, within the esophagus or other body lumens. Methods and deployment catheters are also disclosed.

26 Claims, 18 Drawing Sheets

U.S. PATENT DOCUMENTS

| | | | |
|---|---|---|---|
| 3,739,279 A | * 6/1973 | Hollis | 600/302 |
| 4,257,420 A | 3/1981 | Terayama | |
| 4,326,535 A | 4/1982 | Steffel et al. | |
| 4,503,859 A | 3/1985 | Petty et al. | |
| 4,546,436 A | 10/1985 | Schneider et al. | |
| 4,561,450 A | 12/1985 | Bryant | |
| 4,618,929 A | 10/1986 | Miller et al. | |
| 4,748,562 A | 5/1988 | Miller et al. | |
| 4,823,808 A | 4/1989 | Clegg et al. | |
| 4,924,877 A | 5/1990 | Brooks | |
| 4,967,759 A | 11/1990 | Teves | |
| 4,981,470 A | 1/1991 | Bombeck, IV | |
| 4,991,590 A | 2/1991 | Shi | |
| 5,018,529 A | 5/1991 | Tenerz et al. | |
| 5,117,827 A | 6/1992 | Stuebe et al. | |
| 5,127,404 A | 7/1992 | Wyborny et al. | |
| 5,153,584 A | 10/1992 | Engira | |
| 5,247,938 A | 9/1993 | Silverstein et al. | |
| 5,269,789 A | 12/1993 | Chin et al. | |
| 5,297,437 A | 3/1994 | Schneider | |
| 5,301,673 A | 4/1994 | Rabito et al. | |
| 5,368,027 A | 11/1994 | Lübbers et al. | |
| 5,381,800 A | 1/1995 | Angelchik | |
| 5,398,844 A | 3/1995 | Zaslavsky et al. | |
| 5,479,935 A | 1/1996 | Essen-Moller | |
| 5,486,818 A | 1/1996 | Loponen | |
| 5,624,453 A | 4/1997 | Ahmed | |
| 5,720,771 A | 2/1998 | Snell | |
| 5,759,199 A | 6/1998 | Snell et al. | |
| 5,792,153 A | * 8/1998 | Swain et al. | 606/144 |
| 5,833,625 A | 11/1998 | Essen-Moller | |
| 5,836,895 A | 11/1998 | Ramsey, III | |
| 5,843,139 A | 12/1998 | Goedeke et al. | |
| 5,873,369 A | 2/1999 | Laniado et al. | |
| 5,899,931 A | 5/1999 | Deschamp et al. | |
| 5,935,078 A | 8/1999 | Feierbach | |
| 5,984,875 A | 11/1999 | Brune | |
| 6,358,197 B1 | * 3/2002 | Silverman et al. | 600/29 |
| 6,406,498 B1 | * 6/2002 | Tormala et al. | 623/23.75 |

\* cited by examiner

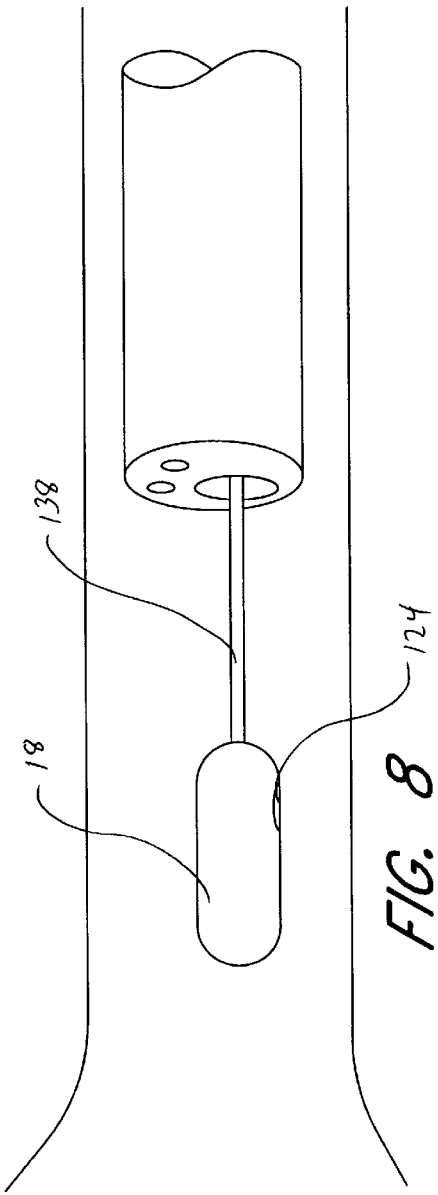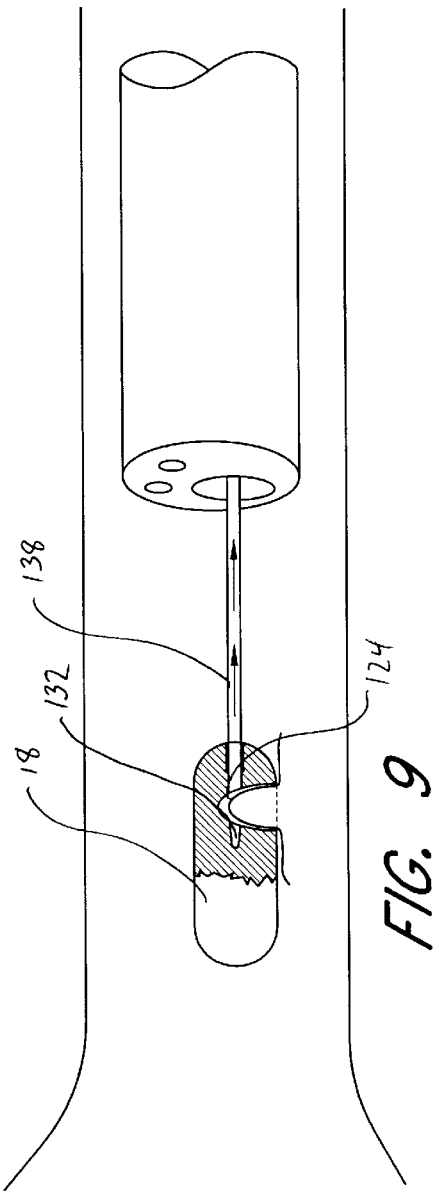

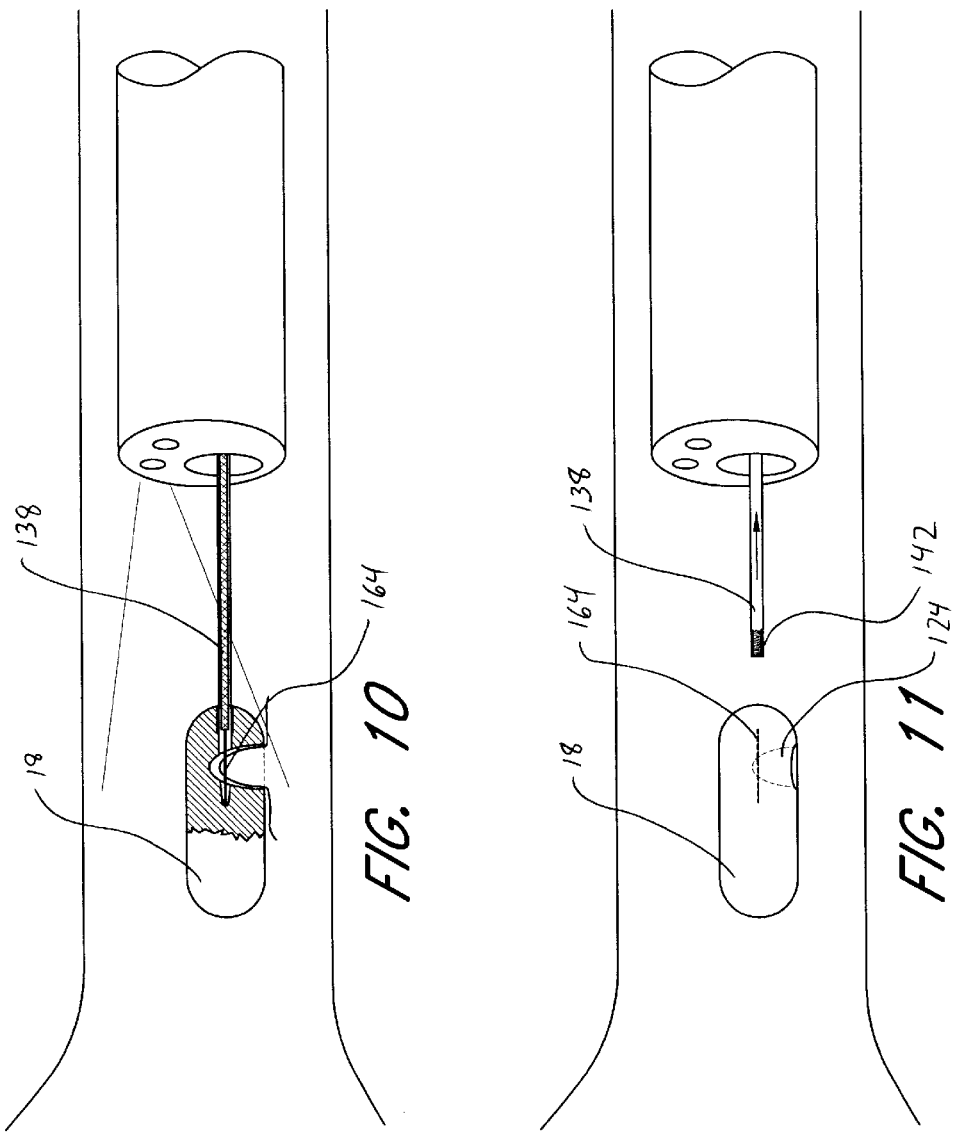

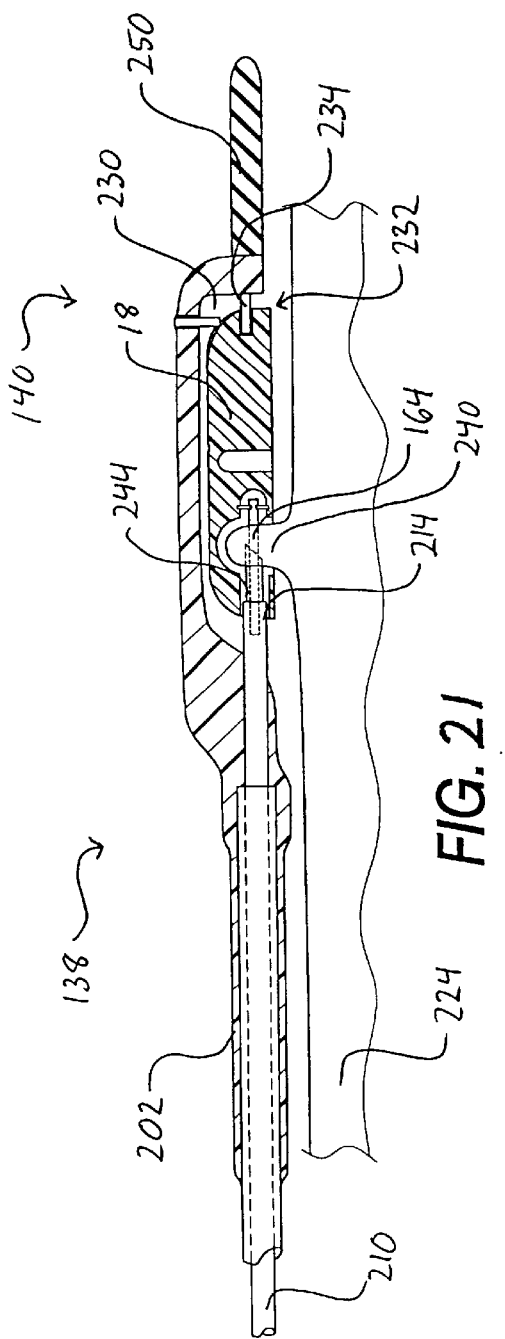
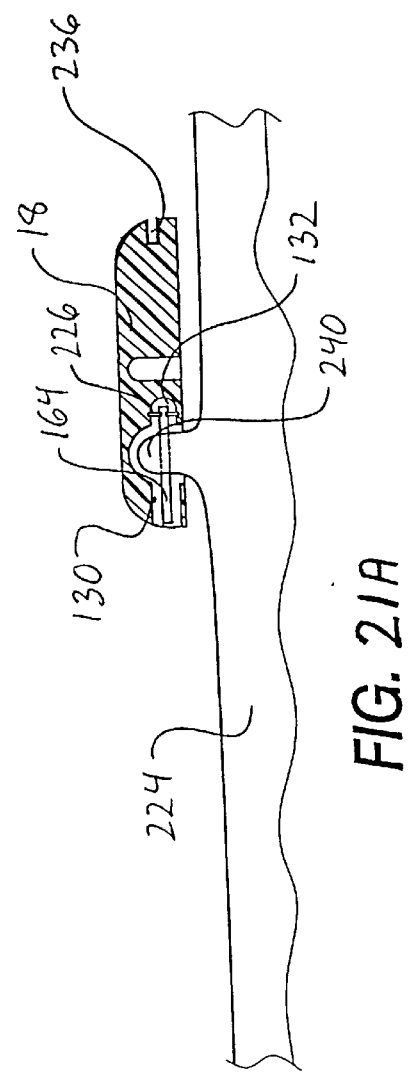
FIG. 21
FIG. 21A

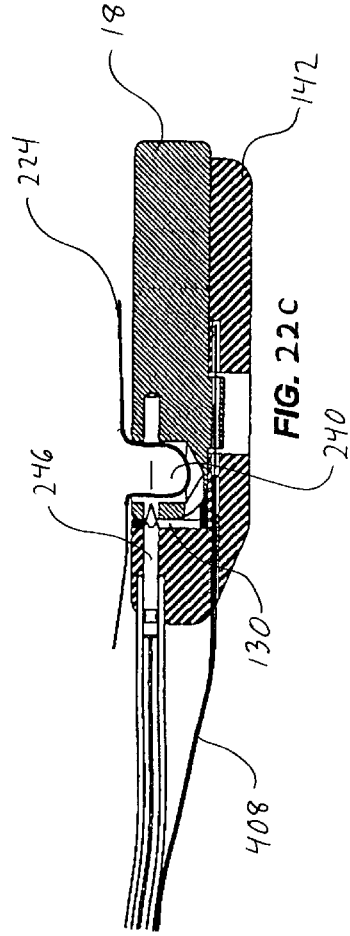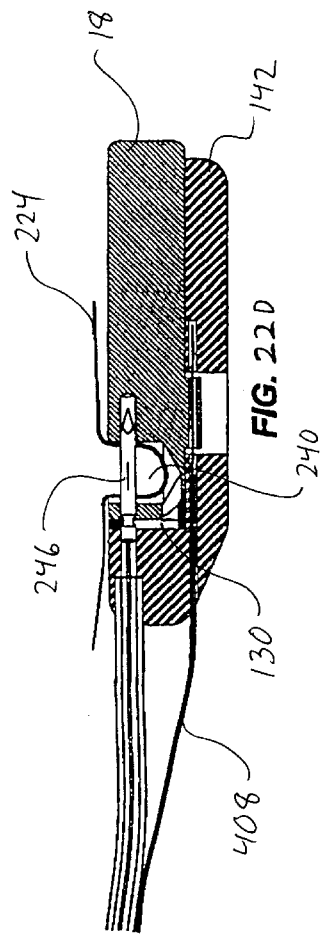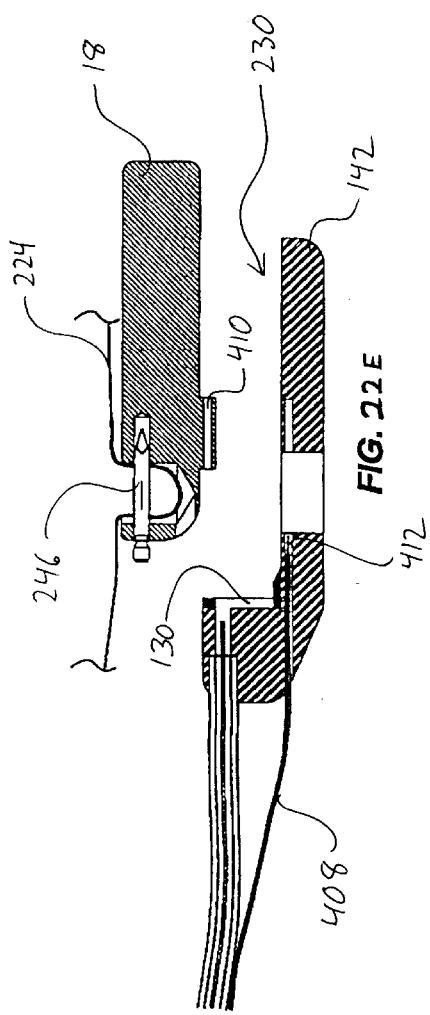

Message Structure

| | Header | | Payload | Trailer |
|---|---|---|---|---|
| Preamble | Transmitter ID | Message ID | Data | Checksum |

Figure 26

ID
IMPLANTABLE MONITORING PROBE

This is a continuation in part of U.S. patent application Ser. No. 09/287,617 filed Apr. 7, 1999 now U.S. Pat. No. 6,285,897.

BACKGROUND OF THE INVENTION

1. Field of the Invention

The present invention relates to minimally invasive physiological monitoring systems. More particularly, the present invention relates to an implantable probe for monitoring one or more parameters in the esophagus, such as pH, in connection with the detection of gastroesophageal reflux disease.

2. Description of the Related Art

Gastroesophageal reflux is a condition in which gastric acid refluxes, or flows in the direction opposite to the normal flow, from the stomach into the esophagus. Frequent reflux episodes may result in a potentially severe problem known as gastroesophageal reflux disease (GERD). GERD is the most common cause of dyspepsia or heartburn. GERD affects approximately 75 million adults in the United States on at least an intermittent basis, and approximately 13 million adults on a daily basis. As a common cause of chest pain, GERD frequently mimics the symptoms of a myocardial infarction or severe angina pectoris, which are signs of severe coronary artery disease. Because their treatments and outcomes are different, distinguishing between GERD and coronary artery disease is of paramount diagnostic importance to the patient and physician.

The lower esophageal sphincter (LES), or valve, is composed of a smooth muscle ring located at the gastroesophageal junction, and it plays a key role in the pathogenesis of GERD. Factors that cause or contribute to GERD include the following: transient relaxation of the LES, delayed stomach emptying, and ineffective esophageal clearance. Another cause of GERD is decreased resting tone of the LES, which produces incompetence (incomplete closing) of the LES.

At rest, the LES maintains a high pressure, between 10 and 30 mm Hg above intragastric pressure. Upon deglutition (swallowing), the LES relaxes before the esophagus contracts, allowing food to pass through into the stomach. After food passes into the stomach, the LES contracts to prevent the stomach contents, including gastric acid, from refluxing into the esophagus. The mechanism of the LES contraction and relaxation is influenced by vagus nerve innervation and hormonal control by gastrin and possibly other gastrointestinal hormones.

Complications of GERD include esophageal erosion, esophageal ulcer, and esophageal stricture. Stricture formation results from scarring of the esophagus following prolonged exposure of the esophageal mucosa to acid reflux. The most common clinical manifestation of stricture is dysphagia (difficulty swallowing). Unlike dysphagia from nonstrictured esophageal reflux, dysphagia caused by stricture is a progressive disorder in that the size of a bolus which can pass into the stomach becomes progressively smaller. Prolonged exposure of esophageal mucosa to acid often leads to a precancerous condition known as Barrett's esophagus. Barrett's esophagus is characterized by the replacement of the normal squamous epithelium that lines the esophagus with abnormal columnar epithelium. Barrett's esophagus is clinically important not only as a marker of severe reflux, but also as a precursor to esophageal cancer.

Efforts have been made to define and report as reflux rapid changes of intraesophageal pH, even while the pH remains within the normal esophageal pH range of 4 to 7. Such pH changes, however, can be difficult to prove to be caused by true gastroesophageal reflux, and in some instances may not be caused by reflux.

Some have measured gastroesophageal reflux with radioisotope techniques. With these techniques, a radiolabeled meal is fed to the patient. With a gamma camera positioned externally on the patient's chest or internally within the esophagus, it is possible to detect gastroesophageal reflux containing the isotope, regardless of pH. The use of radioactive material and the expense of stationary or ambulatory gamma cameras make the radioisotope method for detection of reflux unattractive.

Intestinal impedance has previously been used as a surrogate for measurement of gastric emptying into the intestines. In such studies, a liquid or solid meal is administered to a patient, and changes in intestinal impedance are monitored from external electrodes around the abdomen.

The primary and most reliable method of objectively diagnosing GERD, however, is 24-hour measurement of pH within the lower esophagus. The normal pH range in the esophagus is between 4 and 7. As a general rule, when gastric acid enters the esophagus from the stomach, the intraesophageal pH drops below 4. An epoch of one second or more during which the intraesophageal pH falls below 4 is considered a reflux event.

Certain methods and apparatus are known in the prior art for 24-hour monitoring of intraesophageal pH in patients with suspected GERD. An example of a system for ambulatory 24-hour recording of gastroesophageal reflux is the Digitrapper™ System (manufactured by Synectics Medical AB, in Stockholm, Sweden) used with glass or Monocrystant™ pH catheters (as described in U.S. Pat. No. 4,119,498) and with the analysis software EsopHogram™ (by Gastrosoft, Inc. in Dallas, Tex.). These prior art systems typically measure pH in the esophageal tract with an intraesophageal catheter and generate reports regarding esophageal exposure of gastric juice.

Currently, ambulatory esophageal pH monitoring is performed by passing a pH catheter transnasally into the esophagus, to a point approximately 5 cm above the LES. The proximal end of the nasoesophageal catheter extends outside the patient's nose and is usually taped down to the cheek in two places and draped over the ear.

The use of this indwelling nasoesophageal catheter for ambulatory pH monitoring presents a number of disadvantages. Almost invariably, the catheter's presence is very uncomfortable to patients, who frequently develop a sore throat and rhinorrhea (runny nose) because of local irritation of oropharyngeal and nasopharyngeal mucous membranes, respectively, from the catheter. In addition, many patients are embarrassed to be seen in public with the catheter assembly attached to their faces. Furthermore, patients frequently experience an increased swallowing frequency when the catheter is in place, due to reflex stimulation. This increased swallowing introduces a significant amount of air into the stomach, which can cause abdominal discomfort. Finally, increased swallowing in response to the catheter's presence may erroneously raise a patient's intraesophageal pH readings because saliva is alkaline.

Thus, there remains a need for an ambulatory system that avoids the use of an indwelling nasoesophageal catheter during the assessment of esophageal pH and other physiological parameters to detect gastroesophageal reflux.

SUMMARY OF THE INVENTION

In accordance with one aspect of the present invention, there is provided a monitoring device (sometimes referred to herein as a "probe") for monitoring at least one physiological parameter at an attachment site in a body. The monitoring device comprises a housing, having a tissue attachment surface. A pin is movable from a retracted position to allow the tissue attachment surface to be brought into contact with or adjacent tissue at a preselected attachment site, and an extended position in which it extends through tissue in contact with or adjacent to the attachment surface. The housing carries at least one physiological parameter detector.

In accordance with another aspect of the present invention, there is provided a method of attaching a device to a tissue surface inside of a patient. The method comprises the steps of providing a device having a housing, a concavity on the housing, a window to permit visualization through the housing of the interior of the concavity, and a pin which is axially movable between a retracted position and an extended position which extends at least part way across the concavity. The device is carried on an introduction instrument into the body, and positioned adjacent an attachment site. Tissue is drawn into the concavity, where it may be visualized through the window. The pin is thereafter advanced (proximally or distally) through the tissue to retain the device at the attachment site.

Preferably, the device further comprises a vacuum lumen in communication with the concavity, and the drawing tissue into the concavity step additionally comprises the step of applying suction to the lumen. In one embodiment, the window comprises a transparent wall on the housing, and the visualizing tissue step comprises observing tissue and the pin through the wall of the housing. In one embodiment, the pin comprises a material which degrades or absorbs at the attachment site, and the method further comprises the step of permitting the pin to degrade following a sufficient monitoring period of time, thereby releasing the device from the tissue surface.

In accordance with a further aspect of the present invention, there is provided a method of attaching a device to a tissue surface inside of a patient. The method comprises the steps of providing a device having a housing, a concavity on the housing, and a pin which is axially movable from a retracted position within the housing to an extended position which extends at least part way across the concavity. The device is carried on an introduction instrument into the body, and positioned at an attachment site, such that the concavity is adjacent the tissue surface at the attachment site. Tissue is drawn into the concavity, and the pin is advanced through the tissue to retain the device at the attachment site.

In accordance with a further aspect of the present invention, there is provided a monitoring device for monitoring at least one psychological parameter at an attachment site in a body. The device comprises a housing, having a tissue attachment surface. A pin is movable between a retracted position to allow tissue to be brought into contact with the tissue attachment surface, and an extended position in which the pin extends through the tissue in contact with the attachment surface. The housing carries at least one physiological parameter detector. In one embodiment, the physiological parameter detector comprises a pH detector.

Preferably, the monitoring device further comprises an RF transmitter for transmitting data generated by the physiological parameter detector. Alternatively, the monitoring device comprises an electrical contact for contacting tissue in the body and transmitting data relating to the psychological parameter through the tissue. In one application, the physiological parameter is selected from the group consisting of pH, temperature and pressure. Alternatively, the physiological parameter comprises a concentration of a preselected ion on a tissue surface or within a body fluid. The ion is preferably selected from the group consisting of sodium, potassium, calcium, magnesium, chloride, bicarbonate, and phosphate. In a further aspect of the invention, the physiological parameter comprises the concentration of a solute within a body fluid, such as glucose, biliruben, creatinene, blood urea nitrogen, urinary nitrogen, renin, and angiotensin.

The monitoring device in one embodiment comprises a microprocessor and nonvolatile memory. The microprocessor controls the various functions of the monitoring device circuits. The monitoring device sends a digital signal that is coded to contain a variety of information. The digital message contains code to uniquely identify the monitoring device. This allows multiple devices to be used and inhibits erroneous or stray signal reception. The digital message also indicates what type of information is being sent and a corresponding data packet. The message also includes a checksum to help insure that the data transmission was correctly sent and received.

The monitoring device provides the ability to power itself off and on. This feature conserves battery power and extends the useful life of the monitoring device. The monitoring device also powers up the microprocessor and transmitting circuit up separately from the sensor circuit and alternates the active circuit. This feature further minimizes power consumption and further extends the useful life of the power supply.

Further features and advantages of the present invention will become apparent to those of ordinary skill in the art in view of the detailed description of preferred embodiments, which follows, when considered together with the attached drawings and claims.

BRIEF DESCRIPTION OF THE DRAWINGS

FIG. 8 is a schematic representation of an endoscope having a deployment device and a probe positioned within the esophagus.

FIG. 9 is a schematic illustration as in FIG. 8, with tissue drawn into the tissue cavity.

FIG. 10 is a schematic representation as in FIG. 9 with an attachment pin advanced through the tissue.

FIG. 11 is a schematic representation as in FIG. 10, with the deployment device detached from the probe.

FIG. 21 is a side elevational view as in FIG. 18, showing a transnasal embodiment of the invention.

FIG. 21A is a schematic cross section through a probe, following attachment to a tissue surface.

FIG. 22C is a side elevational view as in FIG. 22B, following application of vacuum to the tissue.

FIG. 22D is a side elevational view as in FIG. 22C, following deployment of the pin.

FIG. 22E is a side elevational view as in FIG. 22D, following retraction of the locking wire and deployment of the probe from the delivery device.

FIG. 26 shows the message structure of the digital messages sent by the monitor to a waiting receiver.

DETAILED DESCRIPTION OF THE PREFERRED EMBODIMENT

The present invention provides a method and system for monitoring physiological parameters within a body lumen (cavity). The invention also comprises methods for attaching a physiological parameter monitor to a wall of a body lumen. The term "lumen" as used herein refers to the space within a tubular wall (e.g., a vessel) or the cavity within a hollow organ. While the invention is described in detail as applied to the human esophagus, those skilled in the art will appreciate that it can apply to other body lumens or cavities, such as those of the stomach, colon, rectum, bladder, uterus, vagina, biliary ducts (including the common bile duct), or blood vessels. The term "esophagus" in this discussion includes the lower esophageal sphincter (LES). Where different embodiments have like elements, like reference numbers are used.

Figure 1:
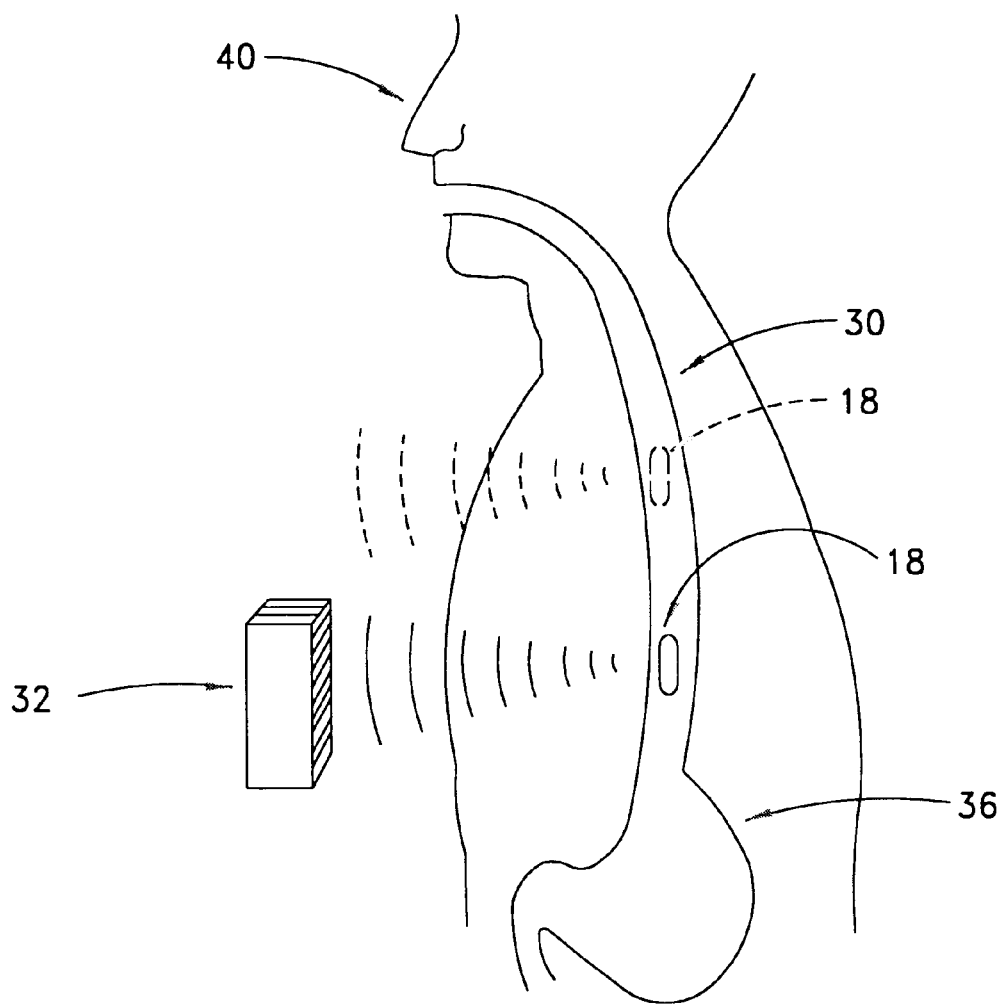
FIG. 1 is a schematic side view of a person with the physiological parameter monitor in place within the esophagus.

FIG. 1 illustrates how physiological parameter data can be relayed by the monitor 18, which is positioned within the esophagus 30, to a radiofrequency receiver 32 (hereinafter "radioreceiver") located outside the body of a person 40. As is illustrated in FIG. 1, more than one monitor 18 can be implanted so that data can be obtained from a plurality of different locations as will be described in greater detail below.

In certain embodiments, this transmission of data is accomplished via radio telemetry in real time. The radioreceiver 32 receives physiological parameter data within 12 seconds after it is measured by the monitor 18. After reception of this data, the radioreceiver 32 apparatus can record, manipulate, interpret and/or display the data, using technology well known to those skilled in the art. In certain embodiments, the patient can wear the receiver 32 and recorder on, for example, a belt, bracelet, arm or leg band, or necklace during the period of pH study or other analysis.

The receiver 32 and recording apparatus can have buttons or other switches thereon that enable the patient or other person to mark certain events in time during the recording period, such as when symptoms occur, when the patient is eating, when the patient is recumbent (either supine or prone), or when the patient is about to sleep. This event marking can be made in any recording medium that is used for recording the physiological parameter, such as magnetic tape or an electronic digital memory chip, in ways that are well known to those of skill in the art.

The monitor 18 can be made to sense the position of the patient, whether horizontal, vertical, or somewhere between horizontal and vertical. Such position sensing can be accomplished through the use of electrical switches that utilize floating fluid bubbles, as used in mechanical level sensing, or electronic gyroscopic techniques as are known to those skilled in the art.

In certain embodiments, the monitor 18 can record and compress physiological parameter data as it is gathered, rather than transmit the data in real time. Following the assessment period, or at intervals therein, an external transceiver can be used to download pulses of condensed data. Transmission of data can be initiated at predetermined intervals or by an activation signal sent from the external transceiver or other activating device to the monitor 18, as will be understood by those of skill in the art. In this manner, a tabletop transceiver can be utilized, either at the patient's home, or in the physician's office or other clinical site.

In other embodiments, the monitor 18 can record, compress, and store physiological parameter data as it is gathered, using a memory chip and microprocessor. The person 40 can excrete the monitor 18 in his or her stool, and the monitor 18 can be retrieved. Subsequently, data stored in the monitor 18 can be downloaded into an external data retrieval device, which can be a computer or other analysis machine located outside the patient's body. This downloading can be accomplished by IR or RF transmission in response to an activation signal, using magnetic field or radiofrequency technology well known to those skilled in the art.

Although the typical gastroesophageal reflux study lasts 24 hours, other time periods for this study can exist, such as 48 hours or longer. Through the use of this invention, it is possible that fewer than 24 hours may be needed to establish the diagnosis of GERD, particularly because real-time monitoring can provide nearly immediate evidence of reflux events. The actual durations of various reflux studies using the present invention will be apparent to those of skill in the art.

Figure 2:
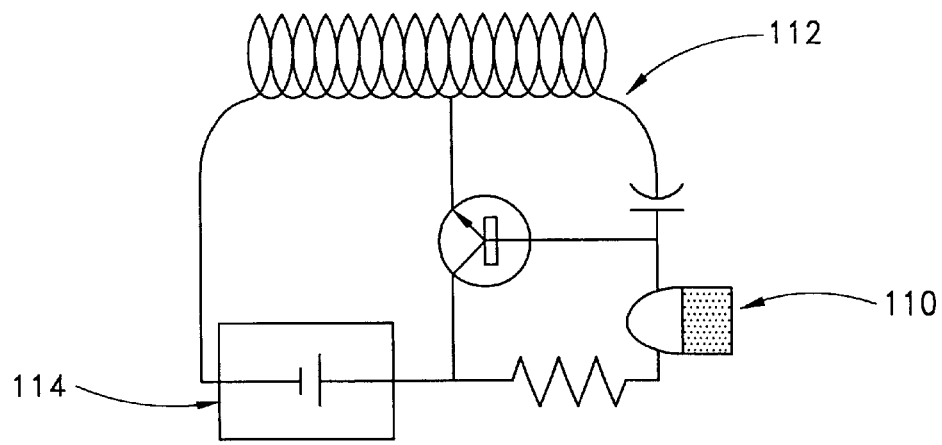
FIG. 2 is a schematic view of one embodiment of an electrical circuit for the physiological parameter monitor.

FIG. 2 illustrates a simplified circuit for a monitor 18 of a physiological parameter (hereinafter "monitor 18"). This monitor 18 may also be referred to as a "probe" or "pill". In the particular embodiment illustrated in FIG. 2, pH is the physiological parameter to be sensed, and it is detected by a transducer 110, which comprises a pH sensor and preferably also a reference sensor. In the present invention, a monitoring transducer (hereinafter "transducer") can be any transducer that senses a physiological parameter and furnishes a signal one of whose electrical characteristics, such as current or voltage, is proportional to the measured physiological parameter.

Although a pH sensor is described here, those skilled in the art will appreciate that a sensor of any of a variety of other physiological parameters, such as pressure or temperature, can be detected and monitored. Sometimes, temperature and/or pressure will be sensed and transduced together with pH, in order to adjust the pH readings and make them more accurate, or to supply additional data helpful in the analysis of the patient's condition. In addition, the concentration of ions or other solutes present in body fluids can be detected and analyzed using this invention. For example, ions such as sodium, potassium, calcium, magnesium, chloride, bicarbonate, or phosphate may be measured. Other solutes whose concentrations in body fluids are of importance and may be measured by the present invention include, among others, glucose, bilirubin (total, conjugated, or unconjugated), creatinine, blood urea nitrogen, urinary nitrogen, renin, and angiotensin. Any combination of two or more of the preceding parameters may be sensed by the transducer 110. For any physiological parameter sensed and transduced by means of a transducer, a reference sensor may or may not be required.

FIG. 2 also illustrates a radiofrequency transmitter circuit 112 and a power source 114. The radiofrequency transmitter circuit 112 can comprise an antenna (or antenna coil), and the antenna can be at least in part external to the monitor shell 120 (seen in FIG. 4). Alternatively, the antenna, if present, can be entirely self-contained within the monitor shell 120. As an alternative to RF transmission, a signal which is indicative of the monitored parameter can be propagated through the patient's tissue from an electrical contact on the probe to a conductive dermal electrode or other conductor in contact with the patient.

When located within the monitor 18, the power source 114 can be a battery or capacitor or any other device that is capable of storing an electrical charge at least temporarily. In a battery powered embodiment, battery life can be extended by disconnecting the battery from other circuit components thereby limiting parasitic current drain. This can be accomplished in a variety of ways, such as by including a magnetically activated switch in the monitor 18. This switch can be used to connect or disconnect the battery as needed. By packaging the monitor 18 with an adjacent permanent magnet, the switch can be opened thereby disconnecting the battery and the shelf life of the device can thus be extended. Removing the monitor 18 from the packaging (and the adjacent permanent magnet) closes the switch and causes the battery to become connected and supply power to the monitor 18.

In alternative embodiments, the source of power to the monitor 18 can be external to the monitor 18 itself. For example, the monitor 18 can derive power from an external electromagnetic radiofrequency (RF) source, as occurs with passive RF telemetry techniques, such as RF coupling, that are well known to those skilled in the art. The monitor 18 can be energized by a time-varying RF wave that is transmitted by an external transceiver 32, also known as an "interrogator," which can also serve as a reader of data from the monitor 18. When the RF field passes through an antenna coil located within the monitor 18, an AC voltage is induced across the coil. This voltage is rectified to supply power to the monitor 18. The physiological parameter data stored in the monitor 18 is transmitted back to the interrogator 32 (FIG. 1), in a process often referred to as "backscattering." By detecting the backscattering signal, the data stored in the monitor 18 can be fully transferred.

Other possible sources of power for the monitor 18 include light, body heat, and the potential difference in voltage that can be generated in body fluids and detected by electrodes made of varying materials. The harnessing of such power sources for biotelemetry purposes is well described in R. Stuart Mackay: *Bio-Medical Telemetry, Sensing and Transmitting Biological Information from Animals and Man,* 2d ed., IEEE Press New York, 1993, whose section entitled "Electronics: Power Sources" is hereby incorporated herein by reference.

Figure 3:
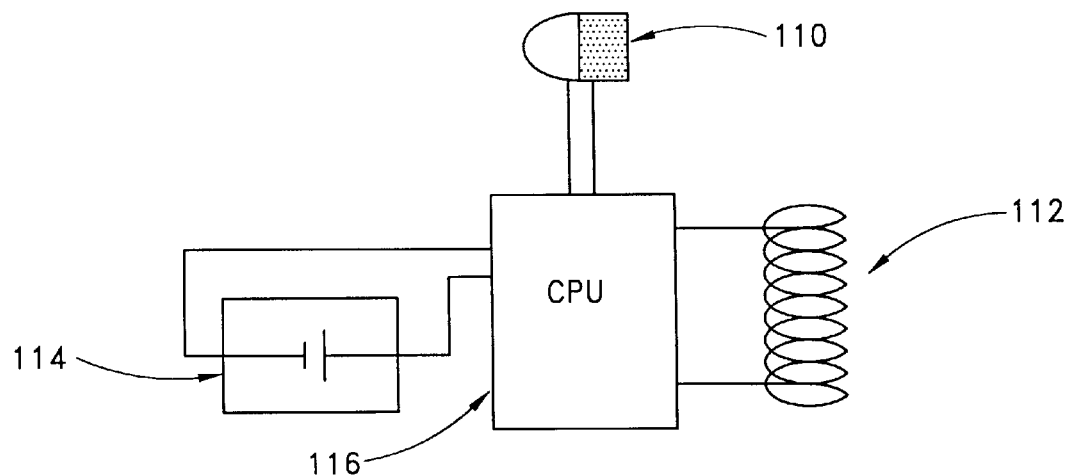
FIG. 3 is a schematic view of a preferred embodiment of the physiological parameter monitor circuit, wherein the circuit also includes a microprocessor.

FIG. 3 illustrates alternative embodiments of the physiological parameter monitor circuitry. In this embodiment, a microprocessor 116, also called a central processing unit (CPU), is illustrated. This microprocessor 116 can perform one or more functions, including temporary storage or memory of data, reception of input signal from the transducer, and transformation between analog and digital signals, among other functions that will be apparent to those skilled in the art. The transducer 110, radiofrequency transmitter 112, and power supply 114 are also present. Many other circuitry components that can help to generate, amplify, modify, or clarify the electrical signal can be used in other embodiments of the monitor. Such components include buffers, amplifiers, signal offset controls, signal gain controls, low pass filters, output voltage clamps, and analog-to-digital converters, among others. Numerous possible circuitry features of a portable pH monitoring device, all of which can be used in the present invention, are well described in U.S. Pat. No. 4,748,562 by Miller, et al., the disclosure of which is incorporated in its entirety herein by reference.

In certain embodiments, the monitor 18 further comprises a digital recorder or memory chip (not illustrated), which records the transduced physiological parameter data. This recorder or memory chip will allow temporary storage of this data accumulated over time (e.g., over a period of 24 hours for a typical gastroesophageal reflux study).

Figure 4:
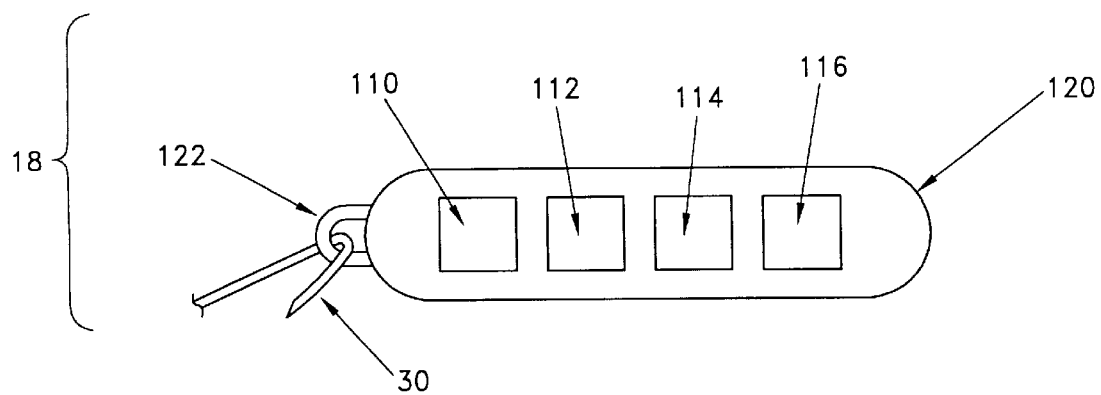
FIG. 4 is a schematic side view of one embodiment of a physiological parameter monitor.

FIG. 4 schematically illustrates the configuration of certain embodiments of the physiological monitor 18. In this embodiment, an outer shell 120 surrounds the monitor's 18 electronic components. The transducer 110, the radiofrequency transmitter 112, the power supply 114, and a microprocessor 116 are encased within the outer shell 120. In certain embodiments, the shape of the shell 120 can resemble that of a pill or gel capsule, as commonly used in various oral drug delivery systems.

The shell 120 can be made of any of various materials, including plastics such as polycarbonates, polyethylene, polytetrafluoroethelyne (Teflon®), nylon, delrin, or polyethylene terephthalate. The material used for the shell 120 should be resistant to water and acidic environments because the shell will be exposed, in some embodiments, to food, water, and gastrointestinal contents, including gastric acid, which is very caustic (with a pH of approximately 1).

The shell 120 can have a lubricious coating applied to its outer surface, which reduces friction between the shell 120 and any object or material that comes in contact with the shell 120, such as the esophageal wall or any food or fluids that flow down the esophagus 30 past the monitor. Such a coating can be made of silicone, silicone derivatives, or other hydrophilic materials that will be apparent to those skilled in the art. This slippery coating on the surface of the shell 120 will reduce the likelihood of occurrence of the following events: (1) ingested material will adhere to the monitor 18, (2) the esophagus 30 will become irritated from repeated contact with the monitor 18 during peristalsis of the esophagus 30, and (3) peristalsis or flowing food or fluid will cause detachment of the monitor 18 from its attachment site.

In certain embodiments, the shape of the shell 120 is streamlined with smooth rounded corners. This feature helps to avoid injury to the gastrointestinal mucosa during endoscopic placement of the monitor 18, while the monitor 18 is attached to the esophagus, and, when the monitor 18 becomes unattached from the esophageal wall, while the monitor 18 passes through the gastrointestinal tract and is excreted in the stool. Preferably, detachment occurs from about 2 days to about 10 days following attachment to the esophageal wall.

The physiological monitor 18 can be placed in the esophagus 30 in a variety of ways. In certain embodiments of the present method, the monitor 18 is placed into the esophagus 30 through the use of a flexible or rigid endoscope 160 inserted through the nose or mouth of the person 40. The monitor 18 can be constrained within or by a deployment device, such as a catheter, until the physician visually verifies attachment through the endoscope 160. Then the monitor 18 can be intentionally deployed and left within the esophagus, using methods known to those of skill in the art.

In other embodiments, a physician can attach the monitor 18 directly to the inner aspect of the esophageal wall through an opening in the esophagus 30 (esophagotomy) or stomach 36 (gastrotomy).

The physiological monitor 18 can be attached to the esophagus 30 in a variety of ways, also referred to herein as "attachment means." In certain embodiments, as shown in FIG. 4, the monitor shell 120 has an eyelet attachment 122, which serves to hold a suture 30, string, staple, or other securing structure, which can secure the monitor to the wall of the esophagus or other body lumen wall. Besides the eyelet attachment 122, many other possible modifications of or attachments to the shell 120, such as one or more loops, rings, brackets, tacks, hooks, clips, strings, threads, or screws, can be utilized to facilitate the attachment or fixation of the monitor to a lumenal wall.

The monitor 18 can, in some embodiments, be attached to the esophagus 30 through the use of a clip, which may resemble, for example, an alligator clip. This clip may or may not utilize a spring mechanism, and it can hold the monitor in place by capturing, or "pinching," the mucosa and submucosa of the esophagus 30 between its arms or "jaws." The clip can have one or more of its parts made of one or more absorbable or dissolvable materials, such as are described below and are known to those skilled in the art. This dissolvable material can facilitate the removal of the monitor 18 from the wall of the esophagus 30 after a given period of time. As materials in the clip dissolve, the tension in the clip that causes it to hold onto, or pinch, the esophagus 30 will eventually decrease, and the clip will break free of the esophagus 30 and travel through the gastrointestinal tract and into the patient's stool.

Figure 5:
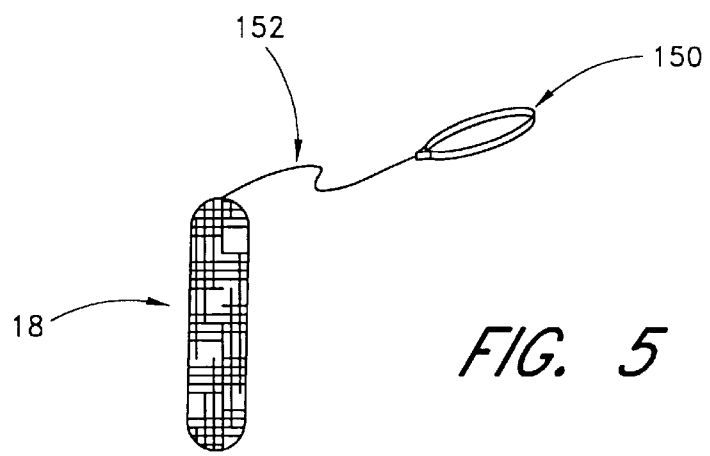
FIG. 5 is a schematic side view of the physiological parameter monitor with an elastic band attached.

In certain embodiments of the present method, as shown in FIG. 5, the monitor 18 is attached to the esophagus 30 by means of a suture loop or an elastic band 150. The elastic band can be attached to the monitor 18 with an absorbable or nonabsorbable suture, string, or thread, otherwise referred to as a "tether" 152. This tether 152 can be made from a variety of materials, such as a polymeric filament, which can be absorbable or nonabsorbable in vivo.

In some embodiments, the tether 152 can be attached to a tooth, such as a molar, of a person. The monitor 18 is thus suspended in the esophagus by the tether 152, which is attached at its other end to the tooth. The attachment to the tooth can be performed by means of an elastic band, plastic band, adhesive materials, or any other means for attaching a structure to a tooth, as are well known in the dental art.

Figure 6:
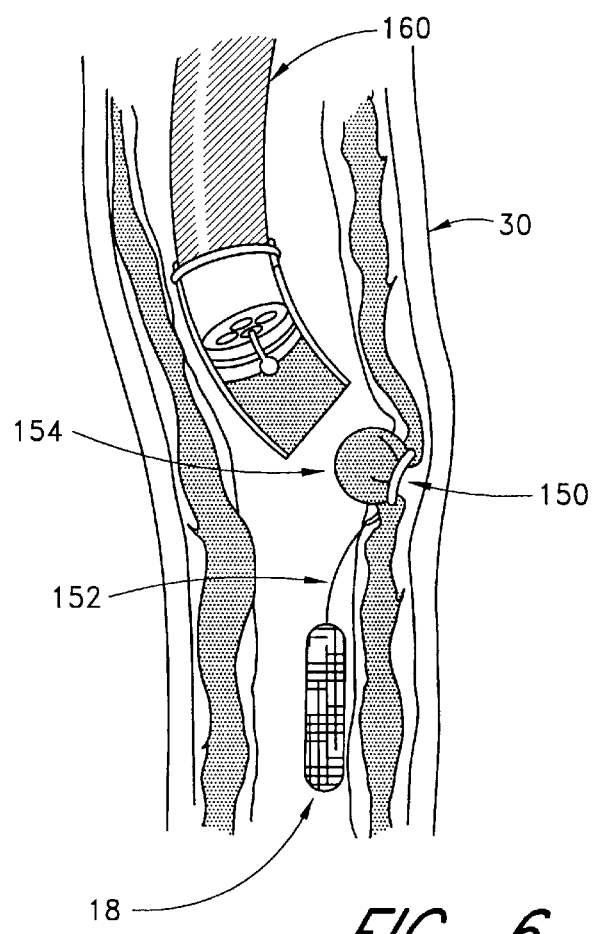
FIG. 6 is a cut-away side view of the esophagus with endoscopic placement of the monitor by means of an elastic band.

As shown in FIG. 6, the elastic band 150 can be placed around a protuberance 154 in the wall of the esophagus 30 or other body lumen. Such a protuberance 154 can be found as a naturally occurring pathological structure, such as a polyp, or it can be formed by a physician (as a "quasi-polyp") using an endoscope 160 by applying suction to the wall of the esophagus 30. Such suction-induced protuberances 154 in the esophagus 30 are well known to those skilled in the art and represent a commonly used method of ligating (tying off) esophageal varices, which are enlarged blood vessels in the wall of the esophagus 30 caused by elevated portal venous pressure.

Although endoscopic ligation techniques typically result in necrosis of the tissue that is elevated into a protuberance 154 and ligated, in the present method the aim of this technique is merely to provide a structure in the lumen of the esophagus 30 or other body lumen upon which to attach temporarily the physiological parameter monitor 18. Thus, it may be desirable not to attach the elastic band 150 to the protuberance 154 too tightly, so as to avoid compromise to the blood supply to the protuberance 154.

In order to avoid exposure of the attachment site to refluxed gastric acid, it will at times be desirable to attach the monitor 18 to the esophagus 30 at a site some significant distance rostral (cephalad) to the LES. The monitor 18 can thereby be suspended from the esophageal attachment site by the tether 152, such that the monitor 18 is positioned close (typically 5 cm superior) to the LES, to facilitate detection of gastroesophageal reflux. This technique optimizes the likelihood that while the monitor 18 is exposed to refluxed gastric acid, the esophageal attachment site is not so exposed because it is sufficiently far from the LES as to avoid the surge of refluxed gastric contents. Distances between the attachment site and the monitor 18 of at least about 0.5 cm, and as much as 10 cm or more, may be utilized for this purpose.

In other embodiments of the present method, the monitor 18 can be attached to the wall of the esophagus 30 or other body lumen using an adhesive substance (hereinafter "adhesive") either alone or in combination with the mechanical attachment structures disclosed herein. This adhesive can be any of a variety of cyanoacrylates, derivatives of cyanoacrylates, or any other adhesive compound with acceptable toxicity to human esophageal cells that provides the necessary adhesion properties required to secure the monitor 18 to the wall of the esophagus 30 for at least a sufficient monitoring period of time. In certain embodiments the monitor 18 can be directly attached to the wall of the esophagus 30 with the adhesive. In other embodiments, the monitor 18 can be attached indirectly, utilizing an intermediate structure, such as an anchor, to which the monitor 18 attaches and which is in turn adhered to the esophagus 30 by means of the adhesive. One example of this type of intermediate structure is an elongate strip of cloth or plastic, secured at one end to the shell 120 and having a tissue attachment surface along its length or at the other end for enhancing adhesive or mechanical bonding to the esophagus 30. Other intermediate structures and materials can be used, as will be apparent to those skilled in the art.

In other embodiments of the present method, the monitor 18 is attached to the esophagus 30 using a self-expandable support structure (not illustrated) that expands or widens to span the diameter of the body lumen, so as to retain the monitor 18 therein. Suitable support structures include self-expandable wire cages, such as are used for supporting grafts in the abdominal aorta and elsewhere in the vascular system. Stents, struts, and other structural devices known to those of skill in the art may be used. Many of these structural devices are used in the fields of vascular radiology and cardiology for the purpose of maintaining patency in blood vessels. These support structures can be made from a variety of materials such as stainless steel, nitinol, or polymeric filament, which can be absorbable or nonabsorbable in vivo.

In further embodiments of the present method, the monitor 18 is attached to the esophagus 30 using one or more sutures, clips, staples, tacks, pins, hooks, barbs, or other securing structures that can at least partially penetrate the mucosa of the esophagus. These securing structures can be made from a variety of materials, including absorbable materials, such as polylactic acid (PLA) or copolymers of PLA and glycolic acid, or polymers of p-dioxanone and 1,4-dioxepan-2-one. A variety of absorbable polyesters of hydroxycarboxylic acids may be used, such as polylactide, polyglycolide, and copolymers of lactide and glycolide, as described in U.S. Pat. Nos. 3,636,956 and 3,297,033, which are hereby incorporated in their entirety herein by reference. The use of absorbable materials allows the securing structure to dissolve or resorb into human tissue after a known or establishable time range, such as 48 to 72 hours, and the monitor 18 can thereby become detached from the esophagus 30 and can then be excreted in the patient's stool.

For example, one or more short pointed barbs can be integrally formed with the shell 120 or secured thereto using any of a variety of attachment techniques which are suitable depending upon the composition of the shell 120 and the barb. This embodiment can be pressed into the wall of the esophagus, thereby causing the barb or barbs to penetrate the mucosa and enter the submucosa. Preferably, any such barbs will not penetrate the muscular wall surrounding the submucosa. Hooks may also be attached to or integrally formed with the shell 120, so that the shell 120 can be hooked onto the wall of the esophagus, possibly in combination with the use of a bioadhesive. Such hooks and barbs may be formed from a bioabsorbable or dissolvable material as has been discussed, to permit detachment of the monitor after a suitable period of time.

In accordance with a further aspect of the present invention, the monitoring device may be provided with a tissue attachment surface adapted for contacting a tissue site. A pin is movable from a retracted position to allow the tissue attachment surface to be brought into contact with or closely adjacent the tissue at the preselected attachment site, and an extended position in which it extends through the tissue adjacent the attachment surface. One embodiment having a concavity at the tissue attachment site is illustrated in FIG. 7.

Figure 7:
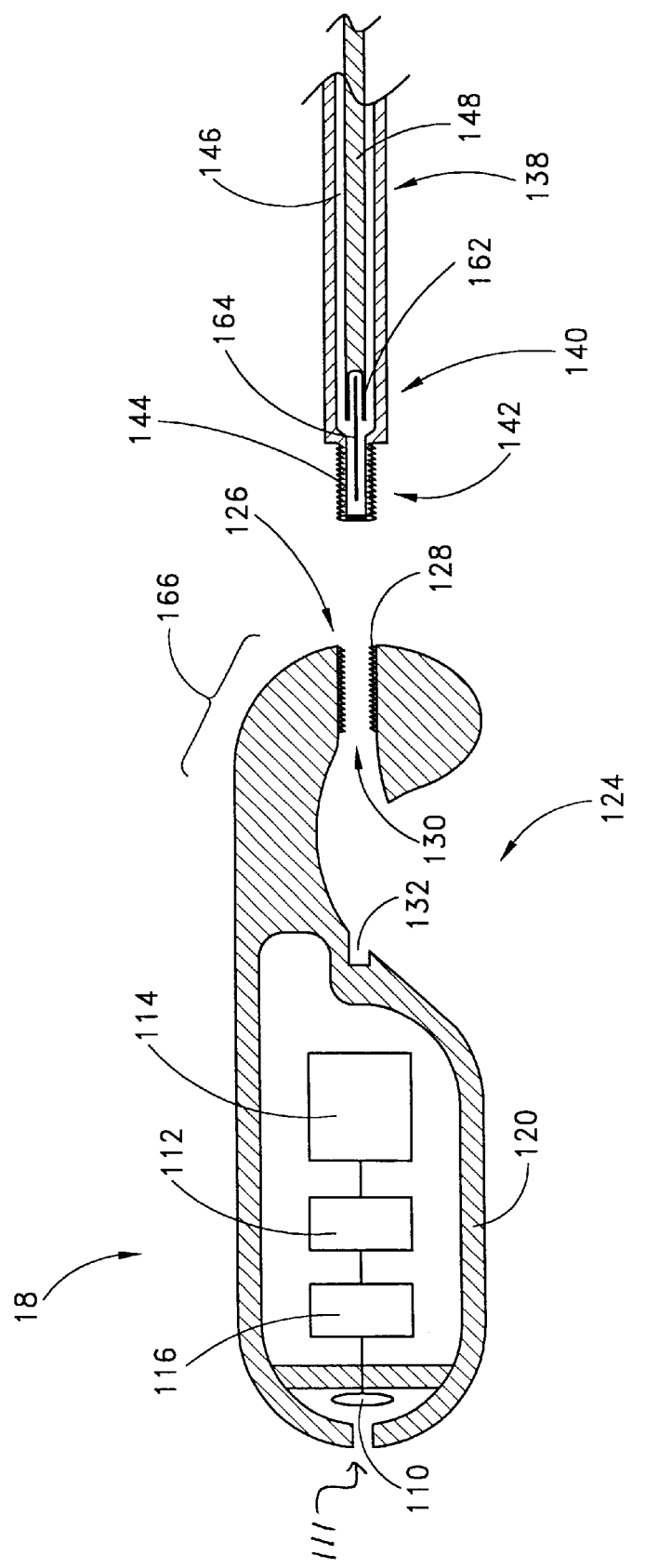
FIG. 7 is a side elevational cross section through an implantable probe in accordance with the present invention, removably attached to a deployment device.

As illustrated in FIG. 7, the monitor or probe 18 is provided with an outer shell 120, for enclosing a transducer 110, such as a pH sensor or other detector as has been described herein. The transducer 110 may be recessed within the shell 120 and exposed to the external environment through a fluid port 111. Alternatively, the transducer 110 may be mounted in the wall of the shell 120, or positioned on the exterior surface of the shell 120, depending upon the nature of the transducer 110 and its fluid contact and surface area requirements. The transducer 110 is in electrical communication with the electronics of the probe 18, such as a transmitter 112, CPU 116 and batteries or other power supply 114 as has been discussed.

The shell 120 is provided with a tissue attachment cavity 124 for receiving tissue at the attachment site. The shell 120 is further provided with a docking structure 126, such as a threaded aperture 128 or other structure for removable connection to a delivery catheter 138. Preferably, the docking structure 126 is in communication with the attachment cavity 124 such as by a vacuum port or other lumen 130. This enables application of a vacuum through the delivery catheter 138 and into the cavity 124, to draw tissue into the cavity 124 as will be discussed below.

The delivery catheter 138 is provided with a proximal end (not illustrated) and a distal end 140. The distal end 140 is provided with a docking structure 142 such as a complimentary thread 144 for removably engaging the threaded aperture 128 on docking structure 126. Any of a variety of alternative releasable docking structures may be utilized, as will be apparent to those of skill in the art in view of the disclosure herein.

The delivery catheter 138 is farther provided with a central lumen 146 having an axially movable plunger 148. Plunger 148 is provided with a distal end 162 having a removable attachment pin 164 carried thereon.

In use, the probe 18 is removably carried by the delivery catheter 138, and may be advanced through the working channel on an endoscope or other access device to an attachment site. Alternatively, the delivery catheter is positioned at the attachment site without the use of a scope. Deployment can be accomplished "blind", using indicia other than visualization. For example, by monitoring psi in a suction (e.g. 15–25 mm Hg) applied to the cavity 124, the presence of tissue at the suction aperture in the cavity 124 can be observed.

The probe 18 is positioned such that the attachment cavity 124 is adjacent the attachment site. A vacuum is applied through the lumen 146, to draw mucosa or other tissue into the attachment cavity 124. Once a sufficient volume of tissue has been drawn into the attachment cavity 124, the plunger 148 is advanced distally to drive the pin 164 through the tissue to pin the probe 18 to the attachment site. In the illustrated embodiment, a pin guide 132, such as a blind lumen, is provided on the distal end of a pin travel path, to further secure the probe 18 at the tissue site. Following deployment of the pin 164, the pin is detached from the distal end 162 of plunger 148, and the delivery catheter 138 is detached from the docking structure 126 on probe 18.

Preferably, the shell 120 is provided with at least a window zone or viewing area 166 to permit endoscopic visualization of the attachment cavity 124. This enables the clinician to view the tissue drawn into the attachment cavity 124, and visually assess the point at which a sufficient amount of tissue has been drawn into attachment cavity 124 to provide an adequate engagement between the pin 164 and the tissue to secure the probe 18 to the attachment site.

Window 166 may be a separate structure, such as a plastic or glass wall which is transparent to visible light. Alternatively, the entire shell 120 may be constructed from a relatively clear material, such as polycarbonate, polysulfone or a thermoset material such epoxy, so that the attachment cavity 124 may be viewed through the opposing side of the shell 120.

The pin 164 may comprise any of a variety of materials such as absorbable or degradable materials discussed above, which will permit the probe 18 to automatically disengage from the attachment site after a period of time. Alternatively, the pin 164 may comprise any of a variety of biocompatible structural materials which are well known in the medical art, such as stainless steel, titanium, high density polyethylenes, nylon, PTFE, or others which are well known in the art.

One method of attaching the probe to the tissue surface is further illustrated by FIGS. 8–11. As illustrated in FIG. 8, the probe 18 is attached to a deployment catheter 138, which extends through the working channel of an endoscope. The endoscope carrying the deployment catheter 138 and probe 18 is transluminally advanced through the esophagus or other body lumen or hollow organ to position the probe 18 at the attachment site. Once positioned at the site, vacuum is applied to the probe to draw mucosa into the chamber. In the illustrated embodiment, the wall of the probe is clear and a viewing zone 166 is provided with a convex curved outer surface to magnify the image of the mucosa within the attachment cavity 124. Alternatively a flat wall may be used.

Depending upon the desired attachment site and other clinical requirements, the deployment assembly may further be provided with one or more steering structures to advance the probe laterally within the lumen, in order to position the attachment cavity 124 sufficiently closed to the mucosal layer to draw mucosa into the attachment cavity 124. For example, the delivery catheter 138 and/or endoscope may be provided with an inflatable balloon on a medial side, which, upon inflation, will advance the probe laterally such that the attachment cavity 124 is firmly positioned against the lateral wall. Axially movable deflection wires and other steering structures are well known in the catheter and endoscope arts, and can be readily incorporated into the delivery catheter 138 as desired. The catheter may also be provided with torque transmission enhancement structures, such as a braided or woven polymeric or metal wall layer.

Referring to FIG. 10, the endoscope is utilized to visualize the mucosa within the attachment cavity 124 following application of vacuum. Preferably, sufficient vacuum is applied to cause the mucosa to contact ("wet") the top of the cavity, before the pin is advanced through the tissue. Following deployment of the pin, the deployment catheter is disengage from the probe and removed.

Figure 12:
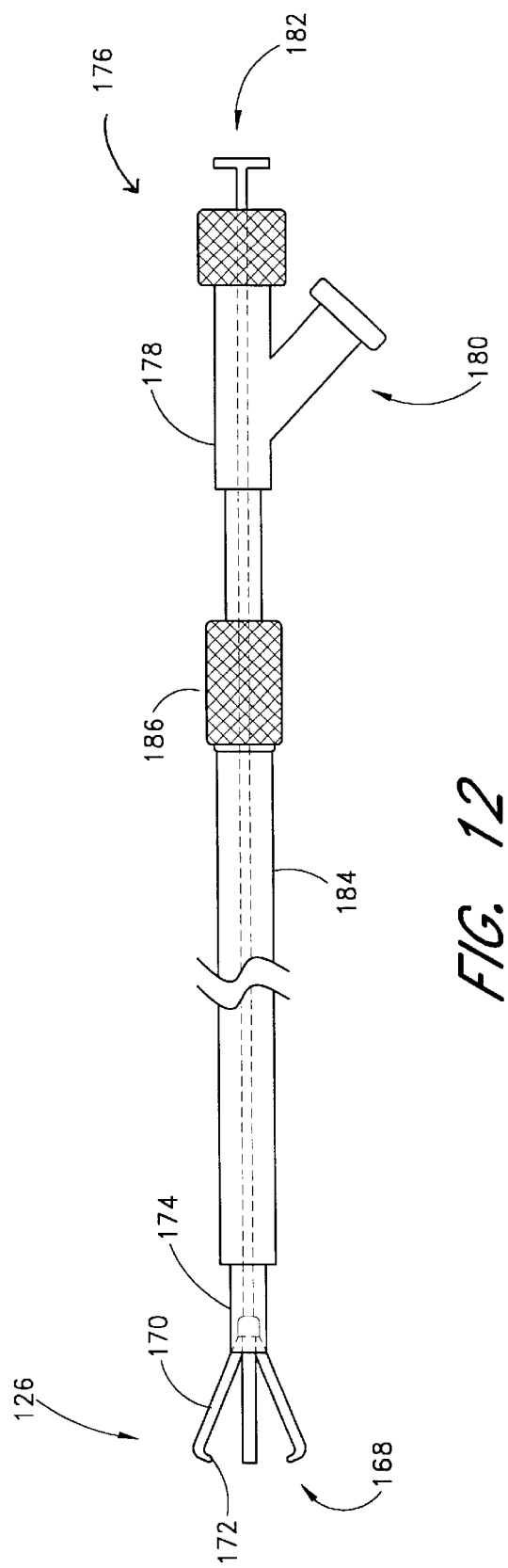
FIG. 12 is a side elevational view of an alternate deployment device in accordance with the present invention.
Figure 13:
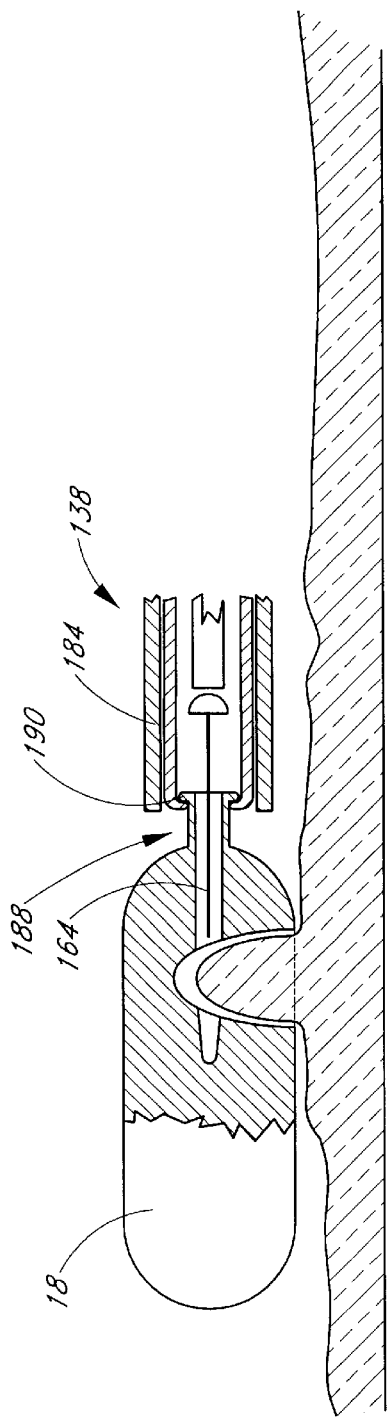
FIG. 13 is a side elevational partial cross section through the distal end of a deployment catheter of the type illustrated in FIG. 12, removably connected to a probe.
Figure 14:
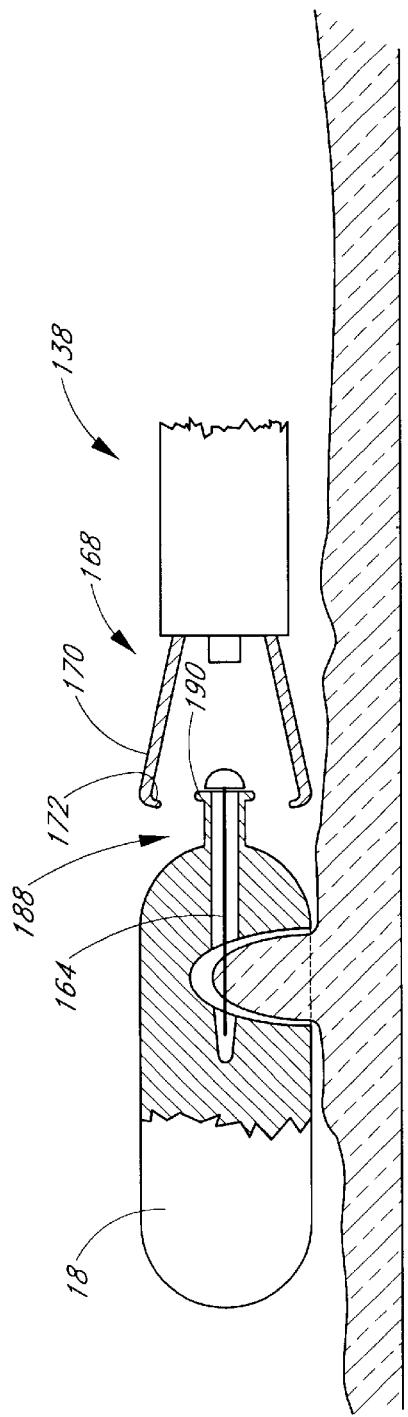
FIG. 14 is a side elevational view as in FIG. 13, with the probe attached to the tissue and the deployment catheter disconnected from the probe.

An alternate delivery catheter is illustrated in FIGS. 12–14. Referring to FIG. 12, the delivery catheter 138 is provided with a docking structure 126 such as a collet 168. Collet 168 comprises two or three or more arms 170 which are movable between a generally axial orientation for grasping the probe and an inclined orientation for releasing the probe. Each arm 170 is provided with a distal attachment surface 172, such as on a proximal face of a radially inwardly directed flange. The arms 170 may be biased radially outwardly from the longitudinal axis of the delivery catheter 138, or may be mechanically linked to a proximal control for opening the collet 168 to release the probe.

The collet 168 is attached to the distal end of a tubular body 174. The proximal end 176 of tubular body 174 is provided with a manifold 178, having a vacuum port 180 and a plunger 182 thereon. Vacuum port 180 is in communication with a central lumen extending through tubular body 174 as has been described, for applying a vacuum to the attachment cavity 124 in probe 18. The plunger 182 is axially movable to deploy a tissue pin 164 through mucosa or other tissue drawn into the attachment cavity 124.

A proximal control 186 may be manipulated to axially proximally retract the movable sleeve 184, to open and close the collet 168. Referring to FIG. 13, the delivery catheter 138 is illustrated with the movable sleeve 184 in a distal position, to lock the collet 168 to the docking structure 126 on probe 18. The proximal projection 188 is provided with one or more radially outwardly extending projections, such as an annular flange 190 for engaging the attachment surfaces 172 on the collet 168.

In this embodiment, the docking structure 126 comprises a proximal projection (188 illustrated as a cylindrical element having a central lumen extending therethrough for both axially movably receiving the pin 164 and providing communication between the central lumen and the attachment cavity 124. Multiple lumen systems may also be devised, in which the pin travels through a different lumen than the vacuum, as will be apparent to those of skill in the art in view of the disclosure herein.

Following deployment of the pin 164, as has been previously discussed, the proximal control 186 is manipulated to proximally retract the sleeve 184, thereby opening collet 168 to release the docking structure 126.

Any of a variety of docking structures can be readily devised, as will be apparent to those of skill in the art in view of the disclosure herein. In general, the docking structure permits a removable attachment of the probe to a deployment catheter. The docking structure permits communication between a vacuum lumen in the deployment catheter and a vacuum pathway in the probe. In addition, the docking structure permits communication between a deployment element in the catheter and a pin adapted to cross at least a portion of the cavity.

The attachment cavity 124 in any of the foregoing probe embodiments can have any of a variety of configurations. Preferably, the depth measured in the radial direction is related to the cross-sectional area of the opening of the cavity in a manner that permits mucosa or other tissue to prolapse into the cavity to a sufficient depth to accomplish the pin function without causing unnecessary trauma to the tissue. In general, depth to opening ratios on the order of about 1:1 are presently contemplated. In general, the tissue opening to the cavity 124 will have an axial length within the range of from about 3 mm to about 5 mm, a width of from about 3 mm to about 5 mm and a depth of from about 3 mm to about 5 mm.

Preferably, the vacuum port or ports between the vacuum lumen and the attachment cavity 124 are positioned sufficiently far away from the opening of the cavity that a sufficient volume of tissue will be drawn into the cavity 124 before occluding the vacuum ports. Two or more ports may be provided, to allow additional application of vacuum following occlusion of the first vacuum port.

Preferably, the opposing surface of the cavity towards which the pin is advanced is provided with a texture or other friction enhancing structure, for assisting to stabilize the tissue during the pin deployment step. Friction enhancing surfaces, such as a plurality of ridges or grooves may be utilized, to assist in retaining tissue while at the same time minimizing trauma.

Figure 15:
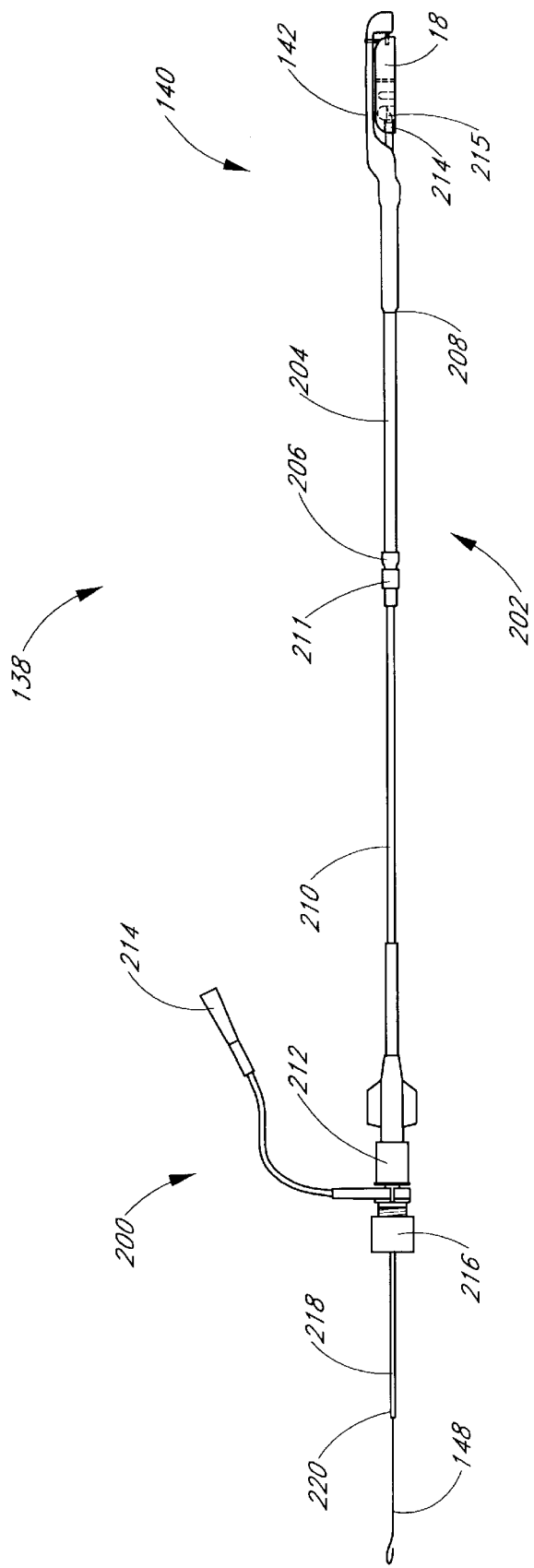
FIG. 15 is a side elevational view of a further embodiment of a deployment device in accordance with the present invention.

Referring to FIG. 15, there is illustrated a side elevational view of an alternate delivery catheter 138 in accordance with the present invention. The delivery catheter 138 comprises a tubular body 202 having a proximal end 200 and a distal end 140. The delivery catheter 138 has an overall length within a range of from about 60 cm to about 80 cm, and a maximum outside diameter through the tubular body 202 of preferably no more than about 3 mm. Construction materials and manufacturing methods for the tubular body 202 as well as other components of the delivery system are well understood in the catheter manufacturing arts.

The tubular body 202 comprises an outer sleeve 204 which extends from a proximal end 206 to a distal end 208. The distal end 208 of outer sleeve 204 is connected to or integrally formed with a docking structure 142, which will be discussed in greater detail below. The proximal end 206 is spaced sufficiently far (proximally) from the docking structure 142 that the proximal end 206 remains outside of the patient during the procedure while the docking structure 142 is at the treatment site. In general, the length of the outer sleeve 204 is from about 30 cm to about 60 cm, and the length of the docking structure 142 is within the range of from about 2 cm to about 10 cm.

An intermediate tube 210 extends axially through the central lumen in outer sleeve 204. Intermediate tube 210 is movably positioned within the outer sleeve 204 such that it can be moved between a first position in which a distal end 214 of intermediate tube 210 removably engages the probe 18, and a second position in which the distal end 214 of intermediate tube 210 is disengaged from the probe 18. A releasable shaft lock 211 is preferably provided to allow the position of the intermediate tube 210 to be locked with respect to the outer sleeve 204, such as to secure the probe 18 within the docking structure 142 during placement. Preferably, the intermediate tube 210 is axially reciprocally movable within the outer sleeve 204 between the first and second positions.

Intermediate tube 210 extends from a manifold 212 to the distal end 214. Manifold 212 may be provided with any of a variety of access ports, depending upon the desired functionality of the delivery catheter 138. In the illustrated embodiment, the manifold 212 is provided with a vacuum port 215. The vacuum port 215 is in communication with a central lumen (not illustrated) within the intermediate tube 210, which communicates with the cavity 124 in probe 18 when the probe is engaged in the docking structure 142. This enables application of vacuum to the vacuum port 215, to draw tissue within cavity 124 in the probe 18 as has been discussed.

Manifold 212 is also preferably provided with an access port which may be provided with a Tuohy Borst valve 216, for axially movably receiving a needle tubing 218. Needle tubing 218 extends throughout the length of the intermediate tube 210, and is advanceable into the cavity 124 as will be discussed.

A pin plunger 148 is axially movably positioned within a central lumen in the needle tubing 218. Pin plunger 148 extends from a proximal end 220 which remains outside of the proximal end of the needle tubing 218, to a distal end which is positioned at or about a distal end 214 of the intermediate tube for reasons which will become apparent. The proximal end of pin plunger 148 may be connected to any of a variety of controls, such as a lever or slider switch.

In one embodiment of the invention, the outer sleeve 204 comprises Teflon, having an axial length of about 60 cm. The intermediate tube 210 comprises nylon, having an axial length of about 80 cm. Both the outer sleeve 204 and intermediate tube 210 may be extruded from any of a variety of materials well known in the catheter arts.

The manifold 212 is preferably injection molded, in accordance with well known techniques. Needle tubing 218 may comprise stainless steel or various polymers such as PET, having an outside diameter of about 0.040 inches, an inside diameter of about 0.020 inches, and an axial length of about 90 cm. The pin plunger 148 comprises 0.014" stainless wire, having a length sufficiently longer than the needle tubing 218 to enable distal deployment of the probe retention pin. Further construction details of the delivery catheter 138 will be apparent to those of skill in the art in view of the disclosure herein.

Referring to FIGS. 16–21A, further details of the docking structure 142 and distal end 140 will become apparent from the discussion of the method of using the delivery catheter 138.

Figure 16:
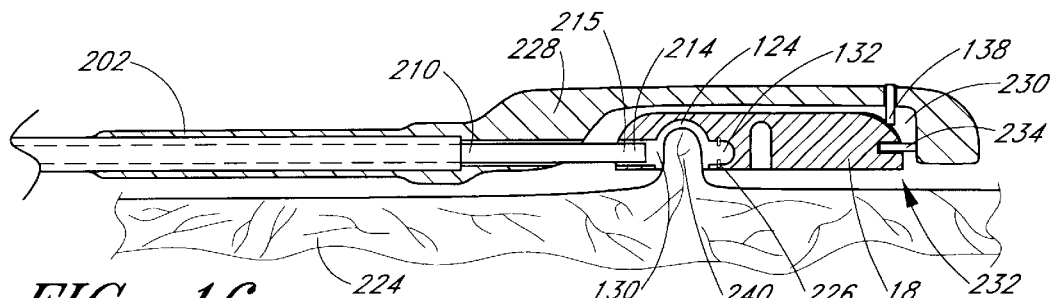
FIG. 16 is an enlarged cross-sectional view through the distal end of the deployment device of FIG. 15, following application of vacuum.

Referring to FIG. 16, the delivery catheter 138 is illustrated in position against the surface of a tissue structure 224, such as the wall of the esophagus. The distal end 214 of the intermediate tube 210 is positioned within a lumen 130 which extends from a proximal end of the probe 18 into the cavity 124. A blind end 132 is also in communication with the cavity 124 as has been discussed. At least one locking structure 226 such as a clip is provided in or near the blind end 132, for retaining the pin as will be discussed.

The probe 18 is releasably retained within the docking structure 142 during the positioning step. Docking structure 142 comprises a body 228 having a concavity 230 thereon for receiving the probe 18. A distal engagement structure 232 such as a proximally extending pin 234 is provided on the docking structure 142, within the cavity 230. Engagement structure 232 may comprise any of a variety of mechanical interfit structures, adapted to cooperate with the distal end 214 of intermediate tube 210 to releasably retain the probe 18 within the cavity 230. In the illustrated embodiment, retention pin 234 extends proximally into a recess 236 on the distal end of the probe 18. One or more guide pins or other guide structures 238 may also be provided, as desired, to retain the probe 18 in the proper position within cavity 230.

FIG. 16 illustrates the delivery catheter 138 in a position such that the probe 18 is in contact with the wall of the tissue structure 224. Vacuum has been applied to vacuum port 215, which is in communication with the cavity 124 by way of intermediate tube 210 and lumen 130. In this manner, a portion 240 of tissue 224 has been drawn within cavity 124.

Figure 17:
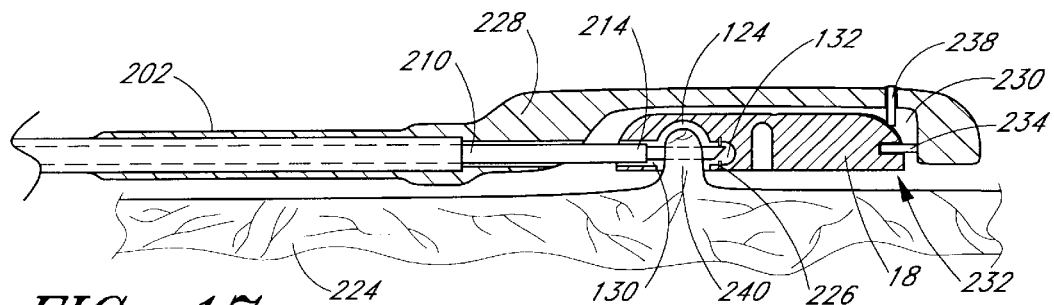
FIG. 17 is a side elevational view as in FIG. 16, following distal advancement of a needle.

Referring to FIG. 17, the needle tubing 218 has been advanced distally within the intermediate tube 210, to advance the distal end 242 of a needle 244 through the tissue portion 240. Needle 244 may comprise a sharpened distal portion of the needle tubing 218, or may comprise a separate needle tip which is secured to the distal end of the needle tubing 218.

Figure 18:
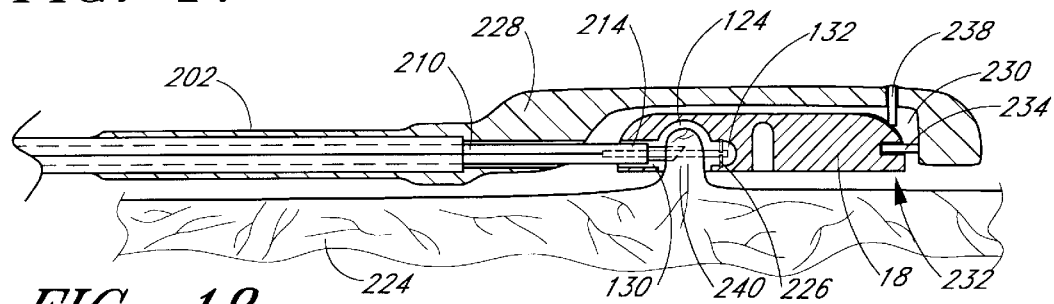
FIG. 18 is a side elevational view as in FIG. 17, following distal advancement of a dowel or pin through the needle.
Figure 19:
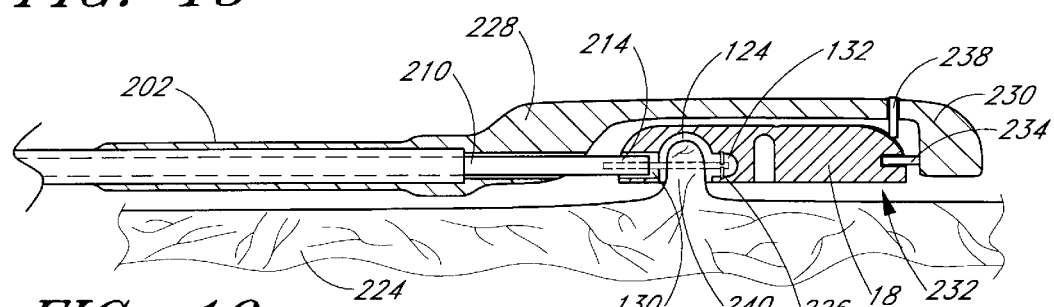
FIG. 19 is a side elevational view as in FIG. 18, following proximal retraction of the needle.
Figure 20:
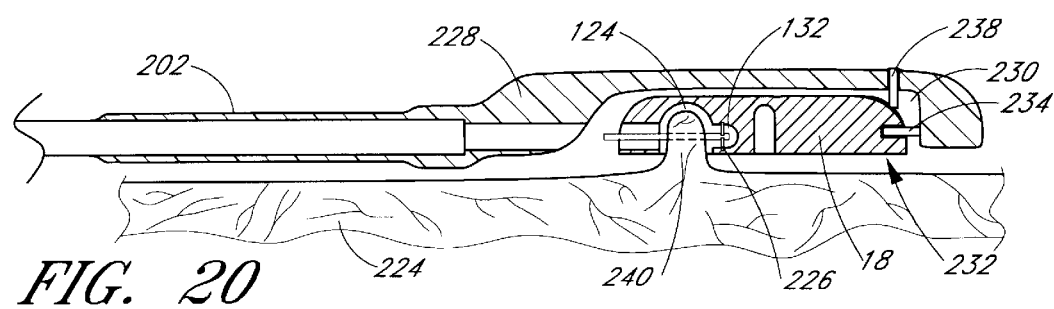
FIG. 20 is a side elevational view as in FIG. 19, following detachment of the docking structure from the probe.

Referring to FIG. 18, the pin plunger 148 is thereafter advanced distally within the needle tubing 218 to advance a pin 246 distally out of the distal end 242 of needle 244. The pin 246 is provided with a complementary surface structure for engaging lock 226. Any of a variety of mechanical interfit locking structures may be utilized, such as an annular recess on the outside surface of pin 246, which engages radially inwardly projecting tabs or flanges in the blind end 132. Alternatively, any of a variety of ramped or ratchet-type interference fit structures may be utilized. The pin has an axial length within the range of from about 3 mm to about 10 mm, and a diameter within the range of from about 0.5 mm to about 2 mm. Any of a variety of materials, such as stainless steel, Nitinol or biocompatible polymers may be used for pin 246.

Following deployment of the pin 246, the needle tubing 218 and pin plunger 148 are proximally retracted to leave the pin 246 in position. Vacuum is disconnected and the intermediate tube 210 is proximally retracted from lumen 130 to disengage the probe 18 from the docking structure 142. The delivery catheter 138 may be advanced slightly distally to disengage the retention pin 234, or other removable locking structure, and the delivery catheter 138 is thereafter removed from the patient leaving the probe 18 in position as shown in FIG. 21A.

Referring to FIG. 21, there is illustrated an alternate embodiment of the delivery catheter 138 at the procedural stage previously illustrated in FIG. 18. In the embodiment of FIG. 21, an elongate flexible distal nose portion 250 is provided on the distal end 140 of the delivery catheter 138. The distal nose 250 comprises a blunt, atraumatic tip, which enables deflection of the docking structure 142 along the soft palette during a transnasal approach. Nose 250 may comprise any of a variety of soft, flexible materials, such as silicone, neoprene, latex, and urethane.

Figure 22A:
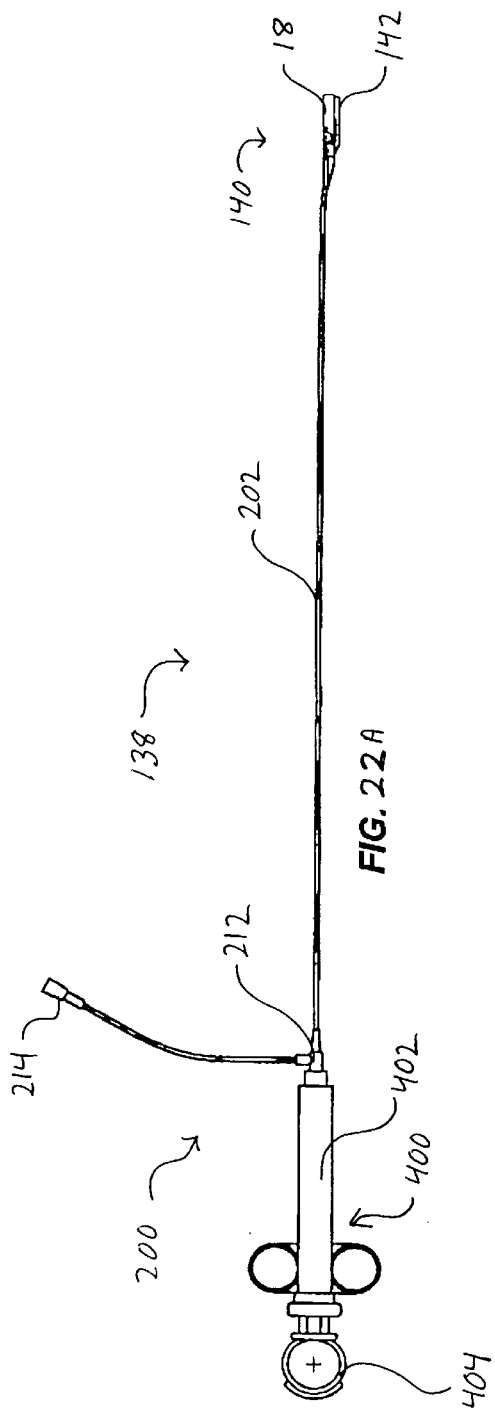
FIG. 22A is a side elevational view of an additional embodiment of a deployment device in accordance with the present invention.
Figure 22B:
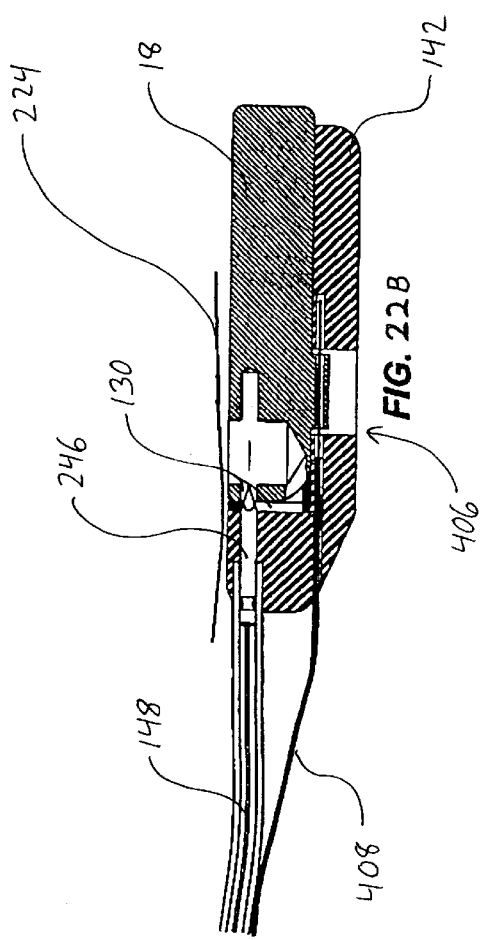
FIG. 22B is an enlarged cross sectional view through the distal end of the deployment device of FIG. 22A, positioned adjacent a tissue surface.

A further embodiment of a delivery catheter 138 is illustrated in FIG. 22A. Details of the distal end 140 including the docking structure 142 are illustrated in FIGS. 22B–22E, which show sequential steps in the deployment of a probe 18.

Delivery catheter 138 illustrated in FIG. 22A is provided with a control 400 on the proximal end 200. Control 400 in the illustrated embodiment comprises a housing 402 and a plunger or other manipulator 404. One or more additional controls may be provided, depending upon the desired functionality of the delivery catheter 138. In the illustrated embodiment, distal advancement of the plunger 404 enables deployment of the pin 246 as has been discussed. Proximal retraction of the plunger 404, or manipulation of other component on control 400 proximally retracts a locking wire 408 to release the probe 18 from the docking structure 142.

In this embodiment, the docking structure 142 is provided with a docking surface on concavity 234 for removably receiving the probe 18. The probe 18 is retained on the docking structure 142 by a lock 406. In the illustrated embodiment, the lock 406 comprises a locking lumen 410 on the probe 18, which, when the probe 18 is positioned on the docking structure 142, aligns with a lumen 412 which removably carries a locking wire 408. See FIG. 22E. As will be seen by reference to FIGS. 22B through 22E, proximal retraction of the locking wire 408 following attachment of the probe 18 to the tissue 224 causes the locking lumen 410 and probe 18 to become disengaged from the docking structure 142.

In addition to measuring pH in the esophagus, the probe 18 may be utilized to measure any of a variety of additional parameters such as esophageal pressure, and a respiratory rate. The probe 18 may also be utilized in the uterus to provide continuous or periodic monitoring of temperature, as a fertility monitor. In a further embodiment, the probe 18 may be utilized in the bladder to measure muscular contraction or pressure waves.

The deployment of the probe 18 may be accomplished under endoscopic visualization as has been discussed. Alternatively, the probe 18 may be introduced "blind" either through the mouth or through the nose. Confirmation that the probe 18 is in an appropriate position for attachment to the esophageal wall in a blind approach may be accomplished by providing a pressure gauge in communication with the cavity 124. Occlusion of the cavity 124 will be observed on the pressure gauge, and provides an indication that tissue has been drawn into the cavity, so that deployment is appropriate.

Alternatively, the monitor 18 may be secured to the wall of the esophagus or other tissue surface by one or more bands which wrap around the monitor 18 and are attached at either end to the tissue surface. Either end of the band may be attached to the tissue surface such as through the use of barbs or hooks, as discussed above. As a further alternative, the monitor 18 may be secured to the tissue surface using a bioabsorbable suture as are known in the art. The suture may be passed through the mucosa, travel laterally through the submucosa and exit the mucosa to form an attachment loop. The suture may travel over the monitor 18 and again travel through the mucosa, along the submucosa and exit the mucosa where it is tied off with the other suture end. This may be accomplished using any of a variety of endoscopic instruments adapted for suturing as will be apparent to those of skill in the art.

In some embodiments, a computer software program is used to analyze the physiological parameter data obtained over a period of time. Such analysis can include graphical representation of the data, identification of abnormal values outside the range of normal (such as pH values outside the range of about 4 to 7, which may represent reflux events), and averaging of data values, among other types of analysis that will be apparent to those skilled in the art.

The method of the present invention may comprise deploying two or three or four or more probes in a single patient, to accomplish any of a variety of objectives. For example, multiple pH probes may be positioned at different axial distances along the wall of the esophagus from the LES, to monitor the change in pH as a function of distance from the LES. Each probe preferably transmits at a unique frequency or with a unique code to enable interpretation of the received data. In this aspect of the invention, each of the multiple probes monitors the same parameter or parameters. In an alternate aspect of the invention, two or more probes may be deployed within a patient such that each probe monitors at least one analyte or parameter that is not monitored by the other probe. Thus, a first probe is positioned at a first site in the body, and detects at least a first parameter. A second probe is positioned at a second site in the body, and measures at least a second parameter. Installation of multiple probes may be accomplished utilizing procedures and devices described above in connection with the installation of a single probe. Data from each of the plurality of probes is preferably transmitted and received in a manner which permits the received data to be attributed to a particular probe. This may be accomplished, for example, by transmitting at different RF frequencies, encoding the data, or any of a variety of other manners which are well understood in the radio frequency transmission arts.

Figure 23:
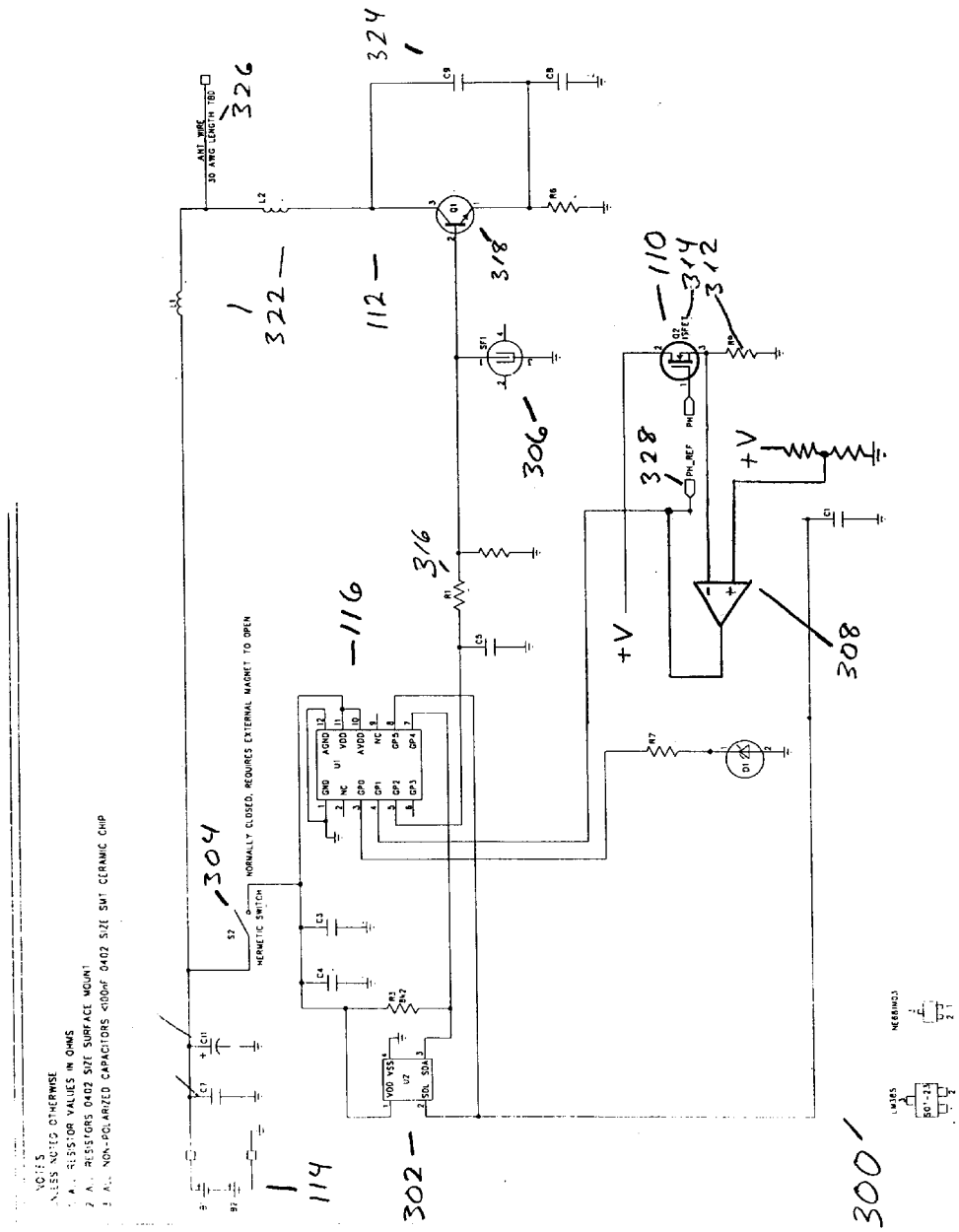
FIG. 23 is a circuit diagram of a preferred embodiment of the physiological parameter monitor circuit, wherein the circuit includes a microprocessor and an ISFET sensor.

FIG. 23 illustrates a circuit diagram of a preferred implementation of a physiological parameter monitor circuit 300. The monitor circuit 300 is contained within the monitor 18 and comprises circuitry to monitor pH, amplify and process the pH measurement, encode a digital message with information including the pH measurement, and transmit the digital message via an RF transmitter 112 in a manner that will be described in greater detail below.

The monitor circuit 300 comprises a power source 114 and a hermetic switch 304. The power source 114 in this embodiment comprises two 5 mm silver oxide coin cells connected in series and a plurality of capacitors that stabilize the output voltage. The hermetic switch 304 is a normally closed, magnetically activated switch. A permanent magnet is placed adjacent the hermetic switch 304 in the shipping packaging of the monitor 18 to open the hermetic switch 304 and disconnect the power source 114 from a microprocessor 116 and non-volatile memory 302. While the monitor 18 is adjacent the permanent magnet in the shipping packaging, the open hermetic switch 304 limits parasitic current drain through the microprocessor 116 and the non-volatile memory 302. When the monitor 18 is removed from the shipping packaging and distanced from the permanent magnet included therein, the open hermetic switch 304 returns to its normally closed position and permits current flow to the monitor circuit 300.

The monitor circuit 300 also comprises a microprocessor 116, also called a central processing unit (CPU). This microprocessor 116 can perform one or more functions, including temporary storage or memory of data, reception of input signals from the transducer, comparison and correction of a signal with respect to a stored or measured reference signal, and transformation between analog and digital signals, among other functions that will be apparent to those skilled in the art. Moreover, in this embodiment, the microprocessor 116 includes an internal clock for tracking a measurement/transmission cycle as will be described in greater detail below. The microprocessor of this embodiment is a type 12C672 available from MicroChip, Inc. of Arizona.

The monitor circuit 300 also comprises non-volatile memory 302. The non-volatile memory is connected to and accessible by the microprocessor 116. The non-volatile memory 302 stores calibration information for the transducer 110. The non-volatile memory 302 also stores the unique identification number for the monitor 18. The non-volatile memory 302 will allow temporary storage of data accumulated over time (e.g., over a period of 24 hours for a typical gastroesophageal reflux study). The non-volatile memory is a type 24LC00 available from MicroChip, Inc. of Arizona.

The monitor circuit 300 also comprises a transducer 110. In this embodiment the transducer 110 is configured to function as a pH sensor. In one embodiment, the transducer 110 comprises an ion sensitive field effect transistor (herein after ISFET) 314. The ISFET 314 is a field effect transistor that is responsive to ambient ion concentration, in this embodiment, H+ ions. The ISFET 314 is switchably driven at a constant voltage by the power source 114. The concentration of H+ions, thereby the pH, in the fluid surrounding the ISFET 314 alters the current flow through the ISFET 314. The current flows through a signal resistor 312 to ground and thus generates an initial pH signal across this signal resistor 312. This initial pH signal is of very low amplitude and is amplified by an amplification circuit 308 before being sent to the microprocessor 116.

The non-inverting input of the amplification circuit 308 is driven through a voltage divider by the microprocessor 116. The pH signal generated by the ISFET 314 across the signal resistor 312 is connected to the inverting input of the amplification circuit 308. The amplified pH signal is sent to the microprocessor 116. The amplified pH signal output from the amplification circuit 308 is also tied to a pH reference 328. The pH reference 328 is a saturated potassium chloride gel that is well known to those skilled in the art. In an alternative embodiment the pH reference 328 can comprise a silver/silver chloride solid state reference.

Hence, the pH level applied to the gate of the ISFET 314 results in a voltage appearing at the resistor 312 that is amplified and combined with the pH reference 328 signal before being sent to the microprocessor 116. As the pH level changes, the voltage at the resistor 312 will also change as will the voltage being sent to the microprocessor 116. In this way, the microprocessor 116 receives a signal that is indicative of the sensed pH level.

The monitor circuit 300 also comprises a transmitter 112. The transmitter 112 receives digital signals from the microprocessor 116 and transmits the signals at a MHz frequency using an amplitude shift keying transmission format in a manner well known to those skilled in the art. The transmitter 112 comprises a RC filter network 316, an oscillator 306, a transistor 318, RF coils 322, biasing network 324, and an antenna 326. The microprocessor 116 sends a serial digital signal that will be described in greater detail below on the GP2 pin through the RC filter network 316. The digital signal is superimposed on the MHz output of the oscillator 306. The combined signal triggers the base of the transistor 318. The transistor 318 is connected to the biasing network 324 and also to the power source 114 through the RF coils 322. The RF coils 322 comprise two inductors connected in series. The connection of the two inductors is also connected to a first end of the antenna 326. The time-varying signal triggering the base of the transistor 318 generates a corresponding time varying current in the RF coils 322 which induces a time varying field that is broadcast via the connected antenna 326.

Figure 24:
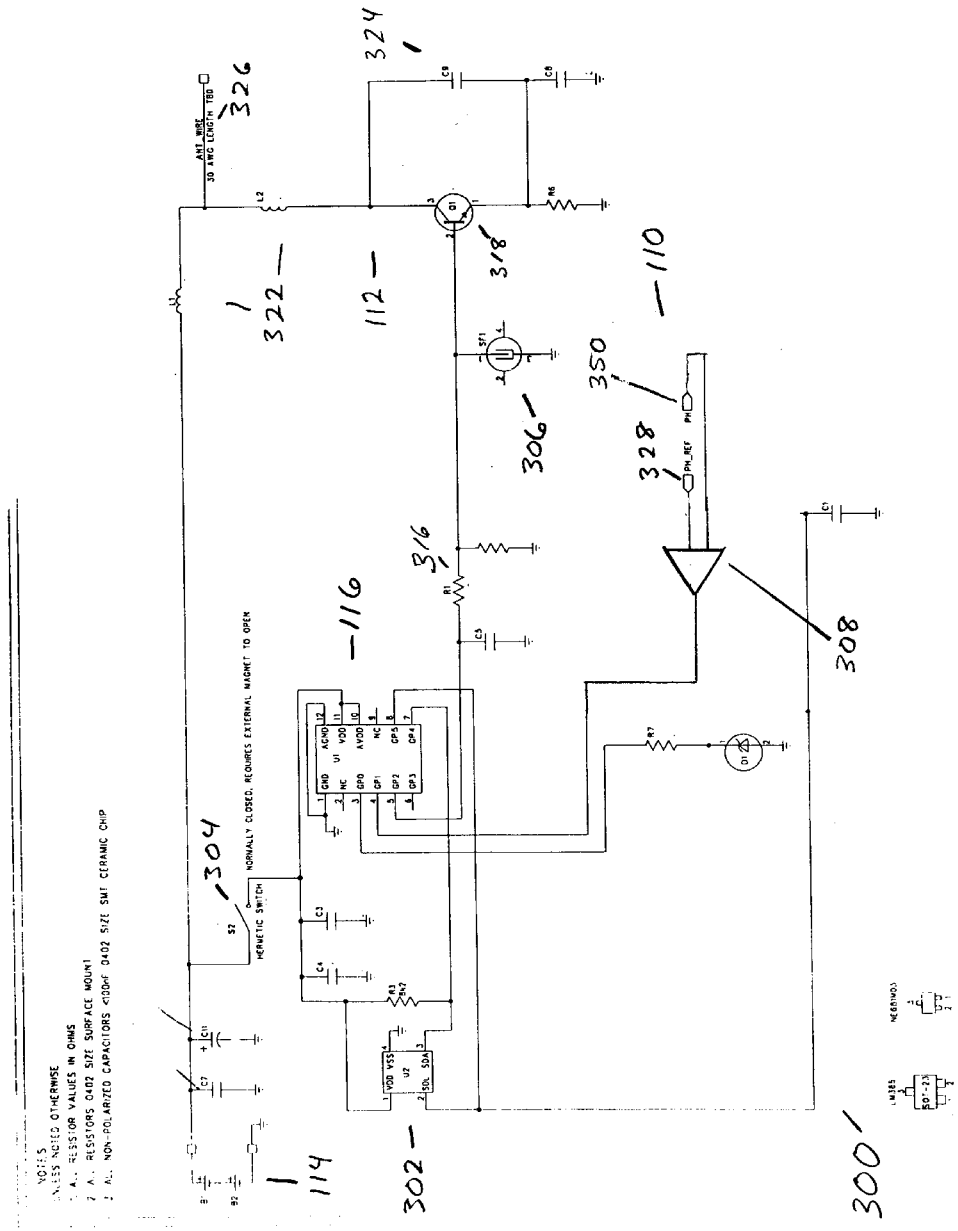
FIG. 24 is a circuit diagram of an alternative embodiment of the physiological parameter monitor circuit, wherein the circuit includes a microprocessor and an antimony sensor.

In an alternative embodiment, the transducer 110 comprises an antimony electrode 350 as shown in FIG. 24. The antimony electrode 350 is a device adapted to measure pH in a manner well known in the art. The monitor circuit 300 of this embodiment is substantially similar to the monitor circuit 300 previously described wherein the transducer 110 comprises the ISFET 314 and signal resistor 312. The antimony electrode 350 and the pH reference 328 are connected to the amplification circuit 308 in a manner well known in the art. The amplification circuit 308 of this embodiment is adapted to provide approximately two to five times signal amplification.

Figure 25:
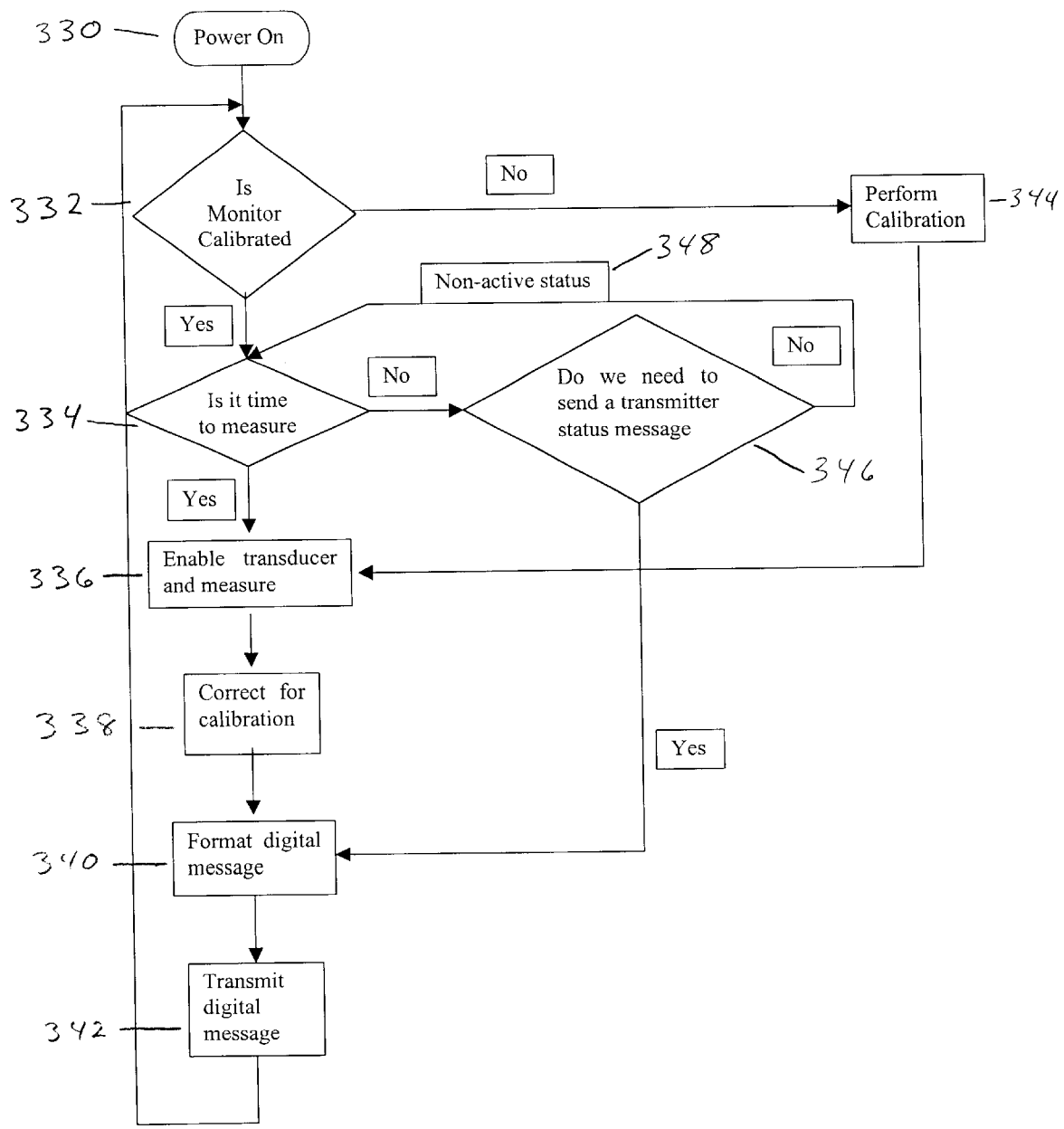
FIG. 25 is a flow chart showing the main functions of the monitor microprocessor.

FIG. 25 shows a flow chart depicting the manner in which the microprocessor 116 controls the operation of the monitor circuit 300. The microprocessor 116 and thereby the monitor circuit 300 has five basic operational states: non-active 348, measurement 336, correction 338, message formation 340, and transmission 342. The microprocessor 116 also has a calibration state 344 that is normally only performed once prior to implanting the monitor 18 in a patient. The microprocessor 116 performs three main decisions: is the monitor 18 calibrated 332, is it time to make a measurement 334, and is a transmitter status message needed 346. The microprocessor 116 conducts a measurement cycle at a variable interval that in this embodiment is approximately every 6 seconds. A transmission cycle is performed by the microprocessor 116 every other measurement cycle, i.e. every 12 seconds in this embodiment.

The monitor circuit 300 initiates operation with a power on 330 state when the monitor 18 is removed from the shipping packaging and distanced from the permanent magnet included therein, which returns the open hermetic switch 304 to its normally closed position and permits current flow to the monitor circuit 300. The microprocessor 116 then performs the calibration decision 332. If the monitor 18 is calibrated the microprocessor 116 performs the measurement decision 334. If the microprocessor 116 determines that it is time to perform a pH measurement, the microprocessor places the monitor circuit 300 into the measurement state 336.

The microprocessor 116 places the monitor circuit 300 into the measurement state 336 by enabling the GP0 pin of the microprocessor 116 which provides power to the transducer 110. The transducer 110 measures the pH, amplifies the signal, and sends the signal to the microprocessor 116 in the manner already described. The measurement state 336 takes approximately 20 ms. After the microprocessor 116 receives the pH measurement signal from the transducer 110, the microprocessor 116 disables the transducer 110. By enabling the transducer 110 for approximately 20 ms out of a 6 second cycle, the monitor circuit 300 realizes significant power savings compared to continuously monitoring the pH and thus significantly extends the power source's 114 useful life.

After the completion of the measurement state 336, the microprocessor 116 enters the correction state 338. The microprocessor 116 calls the non-volatile memory 302 for the calibration values stored therein. The microprocessor 116 then corrects the measured pH signal as needed in a manner well known to those skilled in the art.

Once the microprocessor 116 has completed the correction state 338, the microprocessor 116 enters the message formation state 340. In the message formation state 340, the microprocessor 116 prepares a digital message in a manner that will be described in greater detail below. Once the microprocessor 116 has completed the message formation state 340, the microprocessor 116 enters the transmission state 342. The microprocessor 116 sends the digital message to the transmitter 112 for transmission in the manner previously described.

Once the monitor circuit 300 completes transmitting a digital message, the microprocessor 116 returns to the calibration decision 332 and the measurement decision 334. The correction 338, message formation 340, and transmission 342 states together take approximately 60 ms. A measurement/transmission cycle is performed approximately every 12 seconds. Thus the monitor circuit 300 spends much of its operational time in a non-active state 348. The non-active state 348 refers to the period during which neither the transducer 110 nor the transmitter 112 is active and the microprocessor 116 is in a waiting mode. The non-active state 348 occupies most of the 12 second measurement/transmission cycle. During the non-active state 348, the monitor circuit 300 and the monitor 18 consume a minimum amount of power from the power source 114. In this embodiment, the microprocessor 116 is primarily only operating an internal clock to track the measurement/transmission cycle.

While the microprocessor 116 is performing the measurement decision 334, if a measurement is not needed, the microprocessor 116 monitors whether a transmitter status message is needed in the transmitter status state 346. If the microprocessor 116 determines that a transmitter status message does need to be sent, the microprocessor 116 prepares a digital message containing information about the monitor circuit 300 status in a manner that will be described in greater detail below. The monitor circuit 300 then transmits the status message in the manner previously described.

In order to provide accurate pH measurements, the monitor circuit 300 must first be calibrated. The calibration can be performed at the manufacturer prior to shipment of the monitor 18 or can be performed by the user prior to implantation of the monitor 18 in the patient. Calibration involves comparing the pH value measured by the transducer 110 to that of the pH reference 328 in solutions of known pH and generating correction values. Typically two solutions of known pH are selected and prepared in a manner well known to those skilled in the art.

In the calibration decision 332, the microprocessor 116 checks whether or not the non-volatile memory 302 has calibration values and if it does not, the microprocessor 116 puts itself into calibration state 344. A message is sent to the transmitter 112 to indicate that the monitor circuit 300 is ready for the first solution. The monitor 18 is then placed in the first solution and the monitor circuit 300 measures the pH and prepares a first pH correction value with respect to the pH reference 328. The monitor circuit 300 then sends a message that the monitor circuit 300 has finished calibrating the first solution and is ready for the second solution. The monitor 18 is then typically washed and inserted into the second solution. The monitor circuit 300 measures a second pH value and generates a second pH correction value with respect to the pH reference 328. The monitor circuit 300 then evaluates the calibration values and determines if the calibration procedure was successful. A message is then sent indicating that either the calibration is complete and successful or that calibration errors occurred. Once the calibration procedure is successfully completed, the non-volatile memory 302 stores the calibration information from the pH calibration measurements.

The monitor 18 can be calibrated at the factory before it is packaged for delivery. By pre-calibrating a number of monitors 18 at the factory, each monitor 18 can be more accurately calibrated. The precalibrated monitor 18 is available for immediate use and does not require the user to prepare solutions of known pH or to perform the calibration procedure prior to using the monitor 18. Precalibration provides added economy, greater convenience for the user, and quicker availability for implantation in the patient.

The microprocessor 116 formats digital signals to be transmitted via the transmitter 112. The microprocessor 116 prepares digital messages in the format shown in FIG. 26 in a manner well known to those skilled in the art. The digital message begins with a preamble. The message then includes a header that includes a digital signal identifying the monitor 18. This transmitter ID is stored in and recalled from the nonvolatile memory 302. The header then provides a message ID. The message ID specifies what kind of information is being provided in the digital message. The message ID can indicate that the information provided is the transmitter status, calibration data, or pH measurements. A variable length payload is then included which provides the data specified by the message ID. The digital message concludes with a checksum.

The payload provides the main data of the digital message and is of a variable length depending on what information is being provided. If the transmitter status is being sent, the payload tells whether or not the transmitter is calibrated and whether the power supply 114 voltage is low enough to cause imminent transmitter shut down. The payload also provides information about the current watchdog reset count, the monitor circuit's 300 current transmit count, and the current power supply 114 voltage.

If the message is providing calibration status information, the payload provides information that the monitor circuit 300 is in calibration mode and one of the following states: user is to prepare Liquid 1, the monitor circuit 300 is calibrating Liquid 1, the monitor circuit 300 is finished calibrating Liquid 1 and is ready for the user to prepare Liquid 2, the monitor circuit 300 is calibrating Liquid 2, the monitor circuit 300 has finished calibrating Liquid 2 and has not detected calibration errors, or the monitor circuit 300 has detected calibration errors. The message also provides two calibration values.

If the message is providing pH measurement information, the message gives the last measured pH value. The message also provides the second to last measured pH value.

Once the microprocessor 116 has formatted the message, the message is sent via the GP2 pin of the microprocessor 116 to the transmitter 112 in a serial format in the previously described manner. Once the transmission of the message is complete, the transmitter 112 and the transducer 110 are inactive for the remainder of the measurement/transmission cycle. As previously mentioned, the measurement cycle takes approximately 20 ms. The correction, message formation, and transmission cycles together take approximately 60 ms. Together a complete measurement/transmission cycle takes approximately 80 ms. The monitor circuit 300 is inactive for the remainder of the measurement/transmission period of approximately 12 seconds.

It can be appreciated that by only activating the monitor circuit 300 for approximately 80 ms out of a 12 second period, the monitor 18 consumes appreciably less power than it would by continuous operation and is thereby able to extend the life of the power supply 114. In addition, by alternating the active status of the transmitter 112 and the transducer 110 and having the one not active in an inactive state, the monitor circuit 300 is able to further reduce its power consumption rate and increase the life span of the power supply 114.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. A method of attaching a device to a tissue surface inside of a patient, comprising the steps of:
    providing a device having a housing, a concavity on the housing, a window to permit visualization through the housing of the interior of the concavity, and a pin that is axially movable from a retracted position within the housing to an extended position that extends at least part way across the concavity;
    carrying the device on an introduction instrument into the body;
    positioning the device at an attachment site in the body such that the concavity is adjacent the tissue surface at the attachment site;
    drawing tissue into the concavity;
    advancing the pin through the tissue to retain the device at the attachment site, and
    withdrawing the introduction instrument from the body leaving the pin at the attachment site.

2. A method of attaching a device to a tissue surface inside of a patient as in claim 1, wherein the device further comprises a lumen in communication with the concavity, and the drawing tissue into the concavity step additionally comprises the step of applying suction to the lumen.

3. A method of attaching a device to a tissue surface inside of a patient as in claim 1, wherein the window comprises a transparent wall on the housing, and said visualizing tissue step comprises observing tissue through the wall of the housing.

4. A method of attaching a device to a tissue surface inside of a patient as in claim 1, wherein the carrying the device on an introduction instrument step comprises carrying the device by an endoscope.

5. A method of attaching a device to a tissue surface inside of a patient as in claim 1, wherein the pin comprises a material that degrades at the attachment site, and the method further comprises the step of permitting the pin to degrade, thereby releasing the device from the tissue surface.

6. A method of attaching a device to a tissue surface inside of a patient, comprising the steps of:
    providing a device having a housing, a concavity on the housing, and a pin that is axially movable from a retracted position within the housing to an extended position that extends at least part way across the concavity;
    carrying the device on an introduction instrument into the body;
    positioning the device at an attachment site in the body such that the concavity is adjacent the tissue surface at the attachment site;
    drawing tissue into the concavity;
    advancing the pin through the tissue to retain the device at the attachment site; and
    withdrawing the introduction instrument from the body, leaving the pin at the attachment site.

7. A method of attaching a device to a tissue surface inside of a patient as in claim 6, wherein the device further comprises a lumen in communication with the concavity, and the drawing tissue into the concavity step additionally comprises the step of applying suction to the lumen.

8. A method of attaching a device to a tissue surface inside of a patient as in claim 6, wherein the carrying the device on an introduction instrument step comprises carrying the device on an endoscope.

9. A method of attaching a device to a tissue surface inside of a patient as in claim 6, wherein the pin comprises a material which degrades at the attachment site, and the method further comprises the step of permitting the pin to degrade, thereby releasing the device from the tissue surface.

10. A method of remotely monitoring a physiological parameter in a body lumen of a patient, comprising the steps of:
    providing a device having a housing, a physiological parameter detector in the housing, a concavity on the housing, and a pin that is axially movable from a retracted position within the housing to an extended position that extends at least part way across the concavity;
    carrying the device on an introduction instrument into the body;
    positioning the device at an attachment site in the body such that the concavity is adjacent the tissue surface at the attachment site;
    drawing tissue into the concavity;
    advancing the pin through the tissue to retain the device at the attachment site; sensing at least one physiological parameter; and
    withdrawing the introduction instrument from the body, leaving the pin at the attachment site.

11. A method as in claim 10, wherein the attachment site is the surface of the esophagus.

12. A method as in claim 10, wherein the device further comprises a radiofrequency transmitter, and said physiological parameter data transduced by the detector is transmitted to a radiofrequency receiver and a recording device located outside the patient's body.

13. A method as in claim 10, wherein the device further comprises a microprocessor.

14. A method as in claim 10, wherein the device further comprises a digita recorder that records physiological parameter data.

15. A method as in claim 14, further comprising the step of transferring the physiological parameter data from the digital recorder to an external data retrieval device.

16. A method as in claim 10, wherein the physiological parameter is selected from the group consisting of pH, temperature, and pressure.

17. A method as in claim 16, wherein the physiological parameter data comprises data concerning at least two of said parameters.

18. A method as in claim 16, wherein the physiological parameter data comprises data concerning all three of said parameters.

19. A method as in claim 10, wherein the physiological parameter comprises the concentration of ions within a body fluid.

20. A method as in claim 19, wherein the ions are selected from the group consisting of sodium, potassium, calcium, magnesium, chloride, bicarbonate, and phosphate.

21. A method as in claim 10, wherein the physiological parameter comprises the concentration of a solute within a body fluid.

22. A method as in claim 21, wherein the solute is selected from the group consisting of glucose, bilirubin, creatinine, blood urea nitrogen, urinary nitrogen, renin, and angiotensin.

23. A method as in claim 10, further comprising the step of using a computer and a computer software program to analyze physiological parameter data obtained over a period of time.

24. A method as in claim 23, wherein the pin used for attaching said monitor to the lumen wall is made at least partially of dissolvable materials.

25. A method of attaching a device to a surface of an esophagus, comprising:

providing a device having a housing, a concavity on the housing, and a securing structure that is axially movable from a retracted position within the housing to an extended position which extends at least part way across the concavity;

carrying the device on an introduction instrument into the body;

positioning the device at an attachment site in the esophagus such that the concavity is adjacent the surface at the attachment site;

drawing tissue into the concavity;

advancing the securing structure into the submucosa of the esophagus, without penetrating the muscular wall of the esophagus, to retain the device at the attachment site; and withdrawing the introduction instrument from the body, leaving the securing structure at the attachment site.

26. The method of claim 25, wherein the securing structure comprises a pin.

* * * * *

UNITED STATES PATENT AND TRADEMARK OFFICE
CERTIFICATE OF CORRECTION

PATENT NO. : 6,689,056 B1  Page 1 of 1
APPLICATION NO. : 09/544373
DATED : February 10, 2004
INVENTOR(S) : Kilcoyne et al.

It is certified that error appears in the above-identified patent and that said Letters Patent is hereby corrected as shown below:

Column 24, line 63, delete digita recorder should read – digital recorder

Signed and Sealed this

Twenty-second Day of August, 2006

JON W. DUDAS
*Director of the United States Patent and Trademark Office*